United States Patent [19]

Price et al.

[11] 4,255,440
[45] Mar. 10, 1981

[54] FURAN DERIVATIVES HAVING SELECTIVE ACTION ON HISTAMINE RECEPTORS

[75] Inventors: Barry J. Price, Hertford; John W. Clitherow, Sawbridgeworth; John Bradshaw, Ware, all of England

[73] Assignee: Allen & Hanburys Limited, England

[21] Appl. No.: 951,026

[22] Filed: Oct. 13, 1978

Related U.S. Application Data

[62] Division of Ser. No. 818,762, Jul. 25, 1977, Pat. No. 4,128,658.

[30] Foreign Application Priority Data

Aug. 4, 1976 [GB] United Kingdom .............. 32465/76
Dec. 6, 1976 [GB] United Kingdom .............. 50685/76
May 13, 1977 [GB] United Kingdom .............. 20187/77

[51] Int. Cl.³ .................. C07D 405/06; C07D 413/06; A61K 31/40; A61K 31/535
[52] U.S. Cl. .................. 424/274; 260/326.36; 260/326.5 S; 260/326.5 SF; 260/326.5 D; 260/347.2; 260/347.3; 260/347.7; 424/248.5; 424/248.52; 424/248.53; 424/248.54; 424/250; 424/267; 424/285; 542/416; 544/152; 544/379; 546/214
[58] Field of Search .............. 260/326.36, 326.5 S, 260/326.5 SF, 326.5 D; 546/214; 544/152, 379; 424/274, 267, 248.54, 248.5, 248.52, 248.53, 250; 542/416

[56] References Cited

U.S. PATENT DOCUMENTS

| | | | |
|---|---|---|---|
| 3,097,206 | 7/1963 | Zirkle ............................ | 260/326.36 |
| 3,393,209 | 7/1968 | Majewski ........................ | 260/347.3 |
| 4,000,164 | 12/1976 | Parker ........................... | 260/326.36 |
| 4,110,351 | 8/1978 | Parker ........................... | 260/326.36 |

FOREIGN PATENT DOCUMENTS 1307539 2/1973 United Kingdom .
1338169 11/1973 United Kingdom .
1397436 6/1975 United Kingdom .
1421792 1/1976 United Kingdom .

*Primary Examiner*—Mary C. Lee
*Attorney, Agent, or Firm*—Bacon & Thomas

[57] ABSTRACT

Compounds of the general formula I:

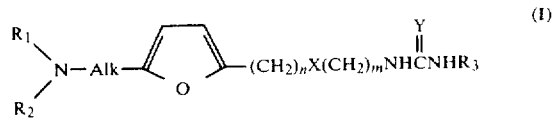

and physiologically acceptable salts thereof and N-oxides and hydrates, in which $R_1$ and $R_2$ which may be the same or different represent hydrogen, lower alkyl, cycloalkyl, lower alkenyl, aralkyl or lower alkyl interrupted by an oxygen atom or a group

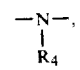

in which $R_4$ represents hydrogen or lower alkyl or $R_1$ and $R_2$ may, together with the nitrogen atom to which they are attached, form a heterocyclic ring which may contain other heteroatoms selected from O and

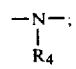

$R_3$ is hydrogen, lower alkyl, lower alkenyl or alkoxyalkyl;
X is $-CH_2-$, $O-$ or $-S-$;
Y represents $=S$, $=O$, $=NR_5$ or $=CHR_6$;
Alk denotes a straight or branched alkylene chain of 1 to 6 carbon atoms;
$R_5$ is H, nitro, cyano, lower alkyl, aryl, alkylsulphonyl, or arylsulphonyl;
$R_6$ represents nitro, arylsulphonyl or alkylsulphonyl;
m is an integer from 2 to 4; and
n is 1 or 2; or when X is $-S-$ or $-CH_2-$, n is zero, 1 or 2.

These compounds have $H_2$-antagonist activity. Intermediates in the production thereof are also provided.

25 Claims, No Drawings

FURAN DERIVATIVES HAVING SELECTIVE ACTION ON HISTAMINE RECEPTORS

This is a division of application Ser. No. 818,762, filed July 25, 1977, now U.S. Pat. No. 4,128,658.

This invention relates to new aminoalkyl furan derivatives having a selective action on histamine receptors, to processes for the preparation thereof and pharmaceutical compositions containing them, as well as their use in therapeutics.

A subdivision of histamine receptors (H-receptors) into two groups designated $H_1$- and $H_2$-receptors has been proposed by Ash and Schild (Brit. J. Pharmacol. Chemother, 1966, 27, 427) and Black et al (Nature 1972, 236, 385). Stimulation of bronchial and gastrointestinal smooth muscle is mediated through $H_1$-receptors and these effects can be prevented by conventional histamine antagonists such as mepyramine. Stimulation of gastric acid secretion and heart rate is mediated through $H_2$-receptors; these effects are not modified by mepyramine but are prevented or abolished by $H_2$-antagonists such as metiamide. Histamine stimulates $H_1$- and $H_2$-receptors.

We have found that certain novel aminoalkyl furan derivatives are selective $H_2$-antagonists, that is they show inhibition of the secretion of gastric acid when this is stimulated via histamine $H_2$-receptors (Ash and Schild loc. cit.). Their ability to prevent the secretion of gastric juice when it is stimulated via histamine $H_2$-receptors can be demonstrated in the perfused rat stomach, using the method described by Ghosh and Schild (Brit. J. Pharmacol. 1958 13 54), modified as hereinafter described and in conscious dogs equipped with Heidenhain pouches using the same method as Black et al (Nature 1972 236 385). The compounds according to the invention do not modify histamine induced contractions of isolated gastrointestinal smooth muscle.

Compounds with histamine $H_2$-blocking activity may be used in the treatment of conditions where there is a hypersecretion of gastric acid e.g. in gastric and peptic ulceration, and in the treatment of allergic conditions where histamine is a known mediator. They may be used, either alone, or in combination with other active ingredients in the treatment of allergic and inflammatory conditions such as urticaria.

The invention therefore provides compounds of general formula (I):

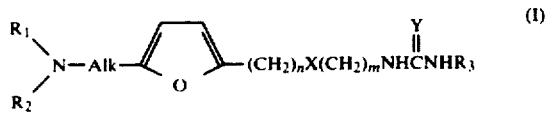

and physiologically acceptable salts and N-oxides and hydrates thereof, in which $R_1$ and $R_2$ which may be the same or different represent hydrogen, lower alkyl, cycloalkyl, lower alkenyl, aralkyl or lower alkyl interrupted by an oxygen atom or a group

in which $R_4$ represents hydrogen or lower alkyl or $R_1$ and $R_2$ may, together with the nitrogen atom to which they are attached, form a heterocyclic ring which may contain other heteroatoms selected from O and

$R_3$ is hydrogen, lower alkyl, lower alkenyl or alkoxyalkyl;
X is $-CH_2-$, $-O-$ or $-S-$
y represents $=S$, $=O$, $=NR_5$ or $=CHR_6$;
Alk denotes a straight or branched alkylene chain of 1 to 6 carbon atoms;
$R_5$ is H, nitro, cyano, lower alkyl, aryl, alkylsulphonyl, or arylsulphonyl;
$R_6$ represents nitro, arylsulphonyl or alkylsulphonyl;
m is an integer from 2 to 4; and
n is 1 or 2; or when X is $-S-$ or $-CH_2-$, n is zero, 1 or 2.

The term 'lower' when applied to alkyl groups means that the group has preferably from 1 to 8 carbon atoms and when applied to alkenyl groups means that the group has preferably 3 to 6 carbon atoms. The term 'aryl' as a group or part of a group preferably means phenyl or phenyl substituted, for example, with alkyl, alkoxy or halogen.

The compounds according to the invention have the advantage that they are readily preparable from readily accessible starting materials.

All the compounds of formula (I) can exhibit tautomerism and the formula is intended to cover all tautomers. Where Alk denotes a branched chain alkylene group, optical isomers may exist, and the formula is intended to cover all diastereoisomers and optical enantiomers.

In a preferred class of compounds according to the invention the following goups have the meanings indicated:
$R_1$ and $R_2$ independently represent hydrogen, alkyl, phenylalkyl, dialkylaminoalkyl or together with the nitrogen atom form a 5- or 6-membered saturated heterocyclic ring e.g. morpholino, piperidino, pyrrolidino, and N-alkylpiperazino.
Alk represents a straight alkylene chain of 1 to 4 carbon atoms.
Y is $=S$, $=O$, $=CHNO_2$ or $=NR_5$ where $R_5$ is hydrogen, nitro, cyano, lower alkyl, alkylsulphonyl or benzenesulphonyl.
X, m, n, and $R_3$ have the meanings given above.

In a particularly preferred class of compounds according to the invention the following groups have the meanings indicated:
$R_1$ and $R_2$ independently represent hydrogen, alkyl of 1 to 3 carbon atoms or phenethyl or together with the nitrogen atom form a pyrrolidine ring.
Alk represents an alkylene chain of 1 to 3 carbon atoms.
Y is $=S$, $=CHNO_2$, or $=NR_5$, where $R_5$ is nitro, cyano, methylsulphonyl or benzenesulphonyl.
$R_3$ represents hydrogen, alkyl of 1 to 3 carbon atoms, propenyl or alkoxyalkyl of 3 carbon atoms.
n+m is 3 or 4, and X is as defined above.

In another preferred class of compounds according to the invention the following groups have the meanings indicated:
$R_1$ and $R_2$ independently represent H, alkyl of 1 to 3 carbon atoms, phenethyl or together with the nitrogen atom form a pyrrolidine ring.

Alk represents an alkylene group of 1 to 3 carbon atoms.

Y is =S, =CHNO$_2$, or =NR$_5$, where R$_5$ is nitro, cyano, methylsulphonyl or benzenesulphonyl.

X is S or —CH$_2$—.

R$_3$ is hydrogen, methyl or methoxyethyl.

n is 1 and m is 2 or 3.

In another particularly preferred class of compounds according to the invention the following groups have the meanings indicated:

R$_1$ is hydrogen, methyl or ethyl.

R$_2$ is methyl or ethyl.

Alk represents a methylene group.

Y is =NCN, =NNO$_2$, or =CHNO$_2$.

R$_3$ is hydrogen or methyl.

X is S or —CH$_2$—.

n is 1 and m is 2.

Particularly preferred specific compounds are:

N-[2-[[[5-(Dimethylamino)methyl-2-furanyl]methyl]thio]ethyl]-N'-methylthiourea

N-Cyano-N'-[2-[[[5-(dimethylamino)methyl-2-furanyl]methyl]thio]ethyl]-N''-methylguanidine N-[2-[[[5-(Dimethylamino)methyl-2-furanyl]methyl]thio]ethyl]-N'-methyl-2-nitro-1,1-ethanediamine N-Cyano-N'-[2-[[[5-(methylamino)methyl-2-furanyl]methyl]thio]ethyl]-N''-methylguanidine N-[2-[[[5-(Diethylamino)methyl-2-furanyl]methyl]thio]ethyl]-N'-methyl-2-nitro-1,1-ethenediamine N-[2-[[[5-(Dimethylamino)methyl-2-furanyl]methyl]thio]ethyl]-N'-(2-methoxyethyl)-2-nitro-1,1-ethenediamine N-[2-[[[5-(Methylamino)methyl-2-furanyl]methyl]thio]ethyl]-N'-methyl-2-nitro-1,1-ethanediamine N-[3-[[5-(Dimethylamino)methyl-2-furanyl]thio]propyl]-N'-methyl-2-nitro-1,1-ethenediamine N-[2-[[[5-(Ethylmethylamino)methyl-2-furanyl]methyl]thio]ethyl]-N'-methyl-2-nitro-1,1-ethenediamine N-[2-[[[5-(Dimethylamino)methyl-2-furanyl]methyl]thio]ethyl]-N'-nitroguanidine N-[2-[[[5-(Dimethylamino)methyl-2-furanyl]methyl]thio]ethyl]-N'-methanesulphonyl-N''-methylguanidine N-[4-[5-(Dimethylamino)methyl-2-furanyl]butyl]-N'-methylthiourea N-Benzenesulphonyl-N'-[2-[[[5-(dimethylamino)methyl-2-furanyl]methyl]thio]ethyl]-N''-methylguanidine N-[5-[5-(Dimethylamino)methyl-2-furanyl]pentyl]-N'-methyl-2-nitro-1,1-ethenediamine N-Cyano-N'-[5-[5-(dimethylamino)methyl-2-furanyl]pentyl]-N''-methyl guanidine N-[4-[5-(Dimethylamino)methyl-2-furanyl]butyl]-N'-methyl-2-nitro-1,1-ethenediamine N-Cyano-N'-[4-[5-(dimethylamino)methyl-2-furanyl]butyl]-N''-methylguanidine N-[2-[[[5-[3-[Dimethylamino]propyl]-2-furanyl]methyl]thio]ethyl]-N'-methyl-2-nitro-1,1-ethenediamine N-[2-[[[5-[[2-(dimethylamino)ethyl]amino]methyl-2-furanyl]methyl]thio]ethyl]-N'-methyl-2-nitro-1,1-ethenediamine The compounds according to the invention readily form physiologically acceptable salts. Such salts include salts with inorganic and organic acids such as hydrochlorides, hydrobromides and sulphates. Particularly useful salts of organic acids are formed with aliphatic mono- or di-carboxylic acids. Examples of such salts are acetates, maleates and fumarates. The compounds may also form hydrates. As indicated the compounds of the invention also include N-oxides, where R$_1$ and R$_2$ are both other than hydrogen.

The compounds according to the invention can be administered orally, topically or parenterally or by suppository, of which the preferred route is the oral route. They may be used in the form of the base or as a physiologically acceptable salt. They will in general be associated with a pharmaceutically acceptable carrier or diluent, to provide a pharmaceutical composition.

The compounds according to the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form. Suitable topical preparations include ointments, lotions, creams, powders and sprays.

A convenient daily dose by the oral route would be of the order of 100 mg to 1.2 g per day, in the form of dosage units containing from 20 to 200 mg per dosage unit. A convenient regimen in the case of a slow release tablet would be twice or three times a day.

Parenteral administration may be by injections at intervals or as a continuous infusion. Injection solutions may contain from 10 to 100 mg/ml of active ingredient.

For topical application a spray, ointment, cream or lotion may be used. These compositions may contain an effective amount of the active ingredient, for example of the order of 1½ to 2% by weight of the total composition.

The compounds of the present invention may be made from a primary amine of the formula:

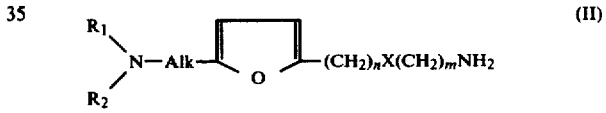

(II)

in which R$_1$, R$_2$, n, X and m have the meanings given herein with a compound capable of introducing the group

in which R$_3$ and Y have the meanings given herein. The amine may be used as the free base or in the form of a salt with a weak acid e.g. acetic acid. Compounds which are capable of introducing the group

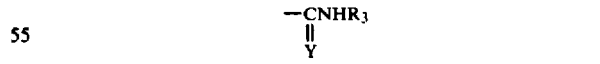

are, isocyanates R$_3$NCO, isothiocyanates R$_3$NCS, or compounds of the formula

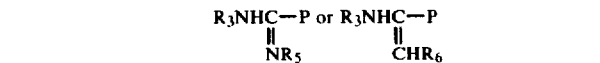

where P is a leaving group. The reaction with the isocyanate or isothiocyanate may be carried out by allowing the amine and isocyanate or isothiocyanate to stand in a solvent such as acetonitrile. The reaction with

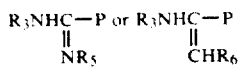

can be carried out by fusing the reactants at an elevated temperature e.g. 100°–120° C. Alternatively the reaction between the amine (II) and

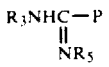

may be carried out in a solvent e.g. acetonitrile at elevated temperatures in the presence of silver nitrate. Alternatively again the amine (II) and the compound

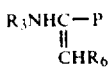

may be stirred in aqueous solution at room temperature. Where $R_3$ represents hydrogen alkali metal cyanates and thiocyanates are used. Examples of leaving groups are halogen, thiomethyl, 3,5-dimethylpyrazolyl or alkoxy, preferably thiomethyl. The introduction of the group

may also be effected by first reacting the amine (II) with a compound of the formula:

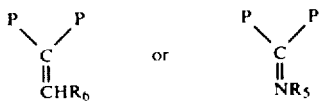

in which P is a leaving group as defined above. This reaction may be effected in a solvent, e.g. ether or acetonitrile at a temperature from ambient to reflux. Treatment of the resulting compound of formula (III):

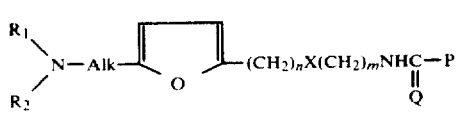

(III)

where Q represents =NR$_5$ or =CHR$_6$ with a primary amine R$_3$NH$_2$ at a temperature from ambient to reflux gives the desired end product.

In an alternative procedure for the production of products in which Y is sulphur, the amine (II) can be heated with carbon disulphide and then reacted with a chloroformate ester, e.g. ethyl chloroformate to form an isothiocyanate (IV) which is then reacted with an amine R$_3$NH$_2$ preferably in an alkanol as solvent e.g. ethanol.

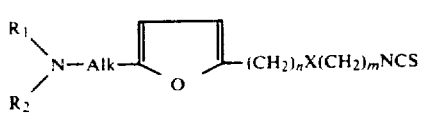

(IV)

In another process, compounds wherein X is sulphur and n is 1, and when R$_1$ and R$_2$ are both hydrogen Y is other than =CHNO$_2$, can be prepared from a starting material of formulae (V) or (VI):

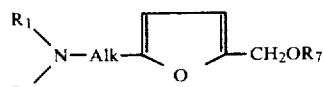

(V)

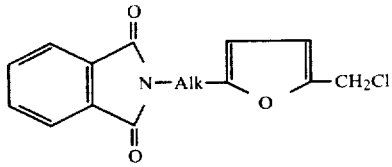

(VI)

(R$_7$ may be hydrogen or an acyl group such as acetyl or p-nitrobenzoyl)

If R$_1$ and R$_2$ in the products are both hydrogen, they may be protected in a compound of formula (V) as, for example a phthalimido group. The above compounds may be reacted with a thiol of formula (VII):

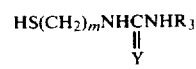

(VII)

with subsequent deprotection where appropriate. When the compound of formula (V) is used the reaction is preferably carried out at 0° C. in concentrated hydrochloric acid. When a compound of formula (VI) is used the reaction may be carried out at room temperature in an organic solvent e.g. dimethylformamide. The chloromethyl compound (VI) may be prepared from the corresponding alcohol using for example, thionyl chloride or concentrated hydrochloric acid.

Products in which Y is a group NCN may be prepared from compounds of formula I where Y is sulphur by heating the latter compounds with a heavy metal cyanamide, such as that of silver, lead, cadmium or mercury preferably in aqueous solution.

Compounds according to the invention in which Y is =NR$_5$ and Alk is a methylene group or branched alkylene chain can also be prepared from compounds of the formula (VIII):

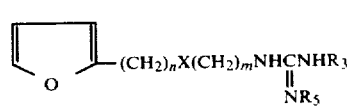

(VIII)

by a Mannich reaction using an appropriate aldehyde and secondary amine or a salt of a primary amine or a secondary amine. For example, the (CH$_3$)$_2$NCH$_2$— group can be introduced using dimethylamine and formaldehyde. The process may be carried out by reacting the amine salt with aqueous formaldehyde and the compound of formula (VIII) or by refluxing the amine salt with paraformaldehyde and the compound of formula (VIII).

In the above discussion of the processes available for the production of the compounds according to the invention reference has been made to primary amines of formula II. These amines are novel compounds and the invention includes such compounds. These intermediates may be made by a number of processes which are described below.

Amines of formula (II) wherein X is S and n is 1 may be prepared from the furfurylthiol of formula (IX):

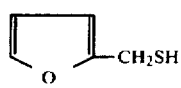

by reaction with an ω-bromoalkylphthalimide (X):

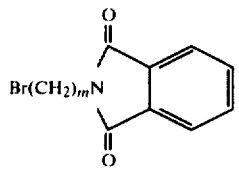

The group

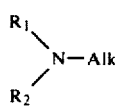

may be introduced into the resulting compound of formula (XI):

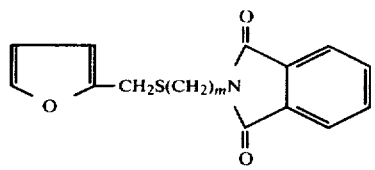

by for example a Mannich reaction.

Removal of the protecting group by reaction with, for example, hydrazine hydrate gives an amine of formula (II).

In an alternative process to amines of formula (II) wherein X is S and n is 1, 2-furfuryl chloride may be used as starting material. The reaction between furfuryl chloride and an ω-aminoalkylthiol in which the amine group is protected, for example as a phthalimide (XII):

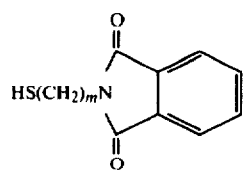

gives an intermediate of formula (XI). This is treated as described above to give an amine of formula (II).

A further process to the amines (II) wherein X is S and n is 1 uses a starting material of formula (XIII):

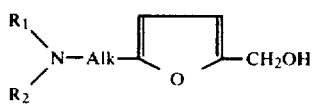

This compound may be treated under acid conditions, with an ω-aminoalkylthiol, in which the amine group may be protected if desired. Alternatively, the compound of formula (XIII) may be converted into the corresponding acetate prior to reaction, under basic conditions with the ω-aminoalkylthiol.

Primary amines of formula II (except those in which X=S and n=zero) may be prepared by reacting furan with butyl lithium, to produce a lithio derivative (XIV):

which is then reacted sequentially with (i) an α,ω-dihalocompound $Hal(CH_2)_nX(CH_2)_mHal$ (where Hal is chlorine, bromine or iodine), and (ii) potassium phthalimide. The product of the reaction of formula (XV):

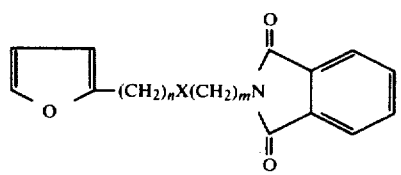

is then subjected to, for example, a Mannich reaction and deprotected by reaction with, for example, hydrazine hydrate.

Intermediates where X is S and n is zero can be made from a furan of formula (XVI):

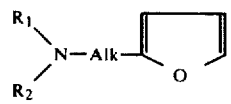

in which neither $R_1$ nor $R_2$ are hydrogen by reacting it with lithium and elemental sulphur followed by reaction with an ω-bromoalkylphthalimide (X). The resulting product of formula (XVII):

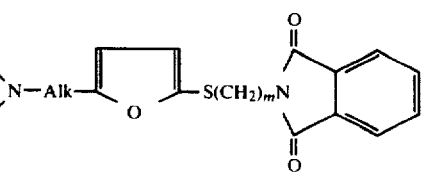

may then be reacted with hydrazine hydrate to remove the protecting group.

The production of an intermediate in which X is an oxygen atom and n is 1 involves reacting an alcohol of the formula (XIII) in a solvent such as dimethylformamide with a compound $Hal(CH_2)_mNH_2$ where Hal represents a halogen atom, preferably chlorine, in the presence of a base, particularly potassium tertiary butoxide.

Intermediates of formula II where m is 2 and X is S or O may also be prepared by using ethylene imine. This compound is reacted with a compound of formula XIII or the isosteric thiol.

Amines of formula II may also be prepared by starting with a compound of formula (XVIII):

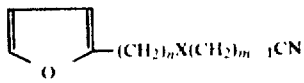 (XVIII)

in which n, m and X have the above stated meanings. A Mannich reaction is carried out on this nitrile compound followed by reduction with lithium aluminium hydride, to give a compound of formula II.

When a Mannich reaction is used, the group

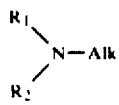

may be introduced at any convenient stage but the reaction is preferably carried out on compounds of formula (XIX) or (XX):

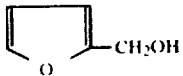 (XIX)

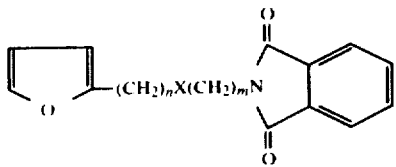 (XX)

The Mannich reaction, using an appropriate aldehyde and amine, is used to prepare compounds in which Alk represents a methylene group or a branched chain alkylene group. Where Alk represents methylene, formaldehyde is used.

An alternative process to compounds wherein Alk is methylene uses furan-2-carboxylic acid as starting material. This is reacted with an amine of formula $R_1R_2NH$ to give an amide of formula (XXI) which is then reduced with, for example, lithium aluminium hydride to give a compound of formula (XXII):

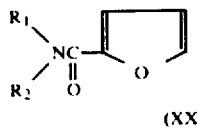 (XXI)   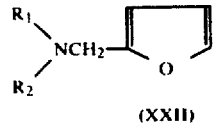 (XXII)

In order to convert a compound of formula XXII into a compound of formula XIII the hydroxymethyl group may be introduced using formaldehyde and acetic acid. If $R_1$ and $R_2$ are both hydrogen, the amino group is protected during hydroxymethylation as a phthalimide. Deprotection is subsequently effected using hydrazine hydrate.

Alternatively, where neither $R_1$ nor $R_2$ are hydrogen, hydroxymethylation may be effected using butyl lithium, followed by formaldehyde.

Where Alk is a straight chain alkylene group containing 2 or more carbon atoms, the following two methods are applicable.

A convenient method used for ethylene derivatives analogous to that above for methylene derivatives using the carboxylic acid (XXIII):

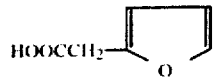 (XXIII)

in place of furan-2-carboxylic acid.

Where the alkylene chain, Alk, is longer than 2 carbon atoms the lithio derivative of formula (XIV) may be treated sequentially with (i) a dihalo alkane of formula Hal Alk Hal where Hal is chlorine, bromine or iodine and (ii) an amine $R_1R_2NH$ to give a compound of formula (XVI) wherein Alk contains 3 to 6 carbon atoms.

Where $R_1$ and $R_2$ are hydrogen, potassium phthalimide replaces the amine $R_1R_2NH$ in both the above reactions. The product of both reactions is hydroxymethylated as described above, followed by deprotection where appropriate to give a compound of formula (XIII).

If compounds where $R_1$ and $R_2$ are other than hydrogen are required, the free amino compounds can be converted into suitable substituted amino groups, for example, by the use of formaldehyde and formic acid by the Eschweiler-Clarke procedure to give the dimethylamino compounds but it is preferable to use the substituted amine at the appropriate stage in the reaction.

Amines of formula II where n is 2 may be made by utilizing as starting material a compound of the formula XXIV:

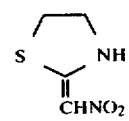 (XXIV)

in which Z is a leaving group, e.g. tosyloxy, mesyloxy or bromine. This compound is reacted with an ω-phthalimidoalkylthiol of the formula (XII). The resultant compound is then subjected to a Mannich reaction and subsequently deprotected to produce the desired amine of formula II.

In producing the compounds of the invention one may react a compound of formula V with a thiol of formula VII in which Y may inter alia be $=CHNO_2$. Compounds of formula VII in which Y is $=CHNO_2$ and m is 2 may be made from a thiazolidine intermediate of the formula:

 (XXV)

by reaction with an amine $R_3NH_2$. The thiazolidine XXV may be made from cysteamine and a bis methylthio compound XXVI:

$$\underset{\underset{CHNO_2}{\|}}{CH_3SCSCH_3} \qquad (XXVI)$$

The thiols of formula VII wherein Y is $=CHNO_2$ and m is 2 are novel compounds and the invention extends also therefore to such compounds and to the above process of making them.

In order that the invention may be more fully understood, the following Examples are given by way of illustration only. Preceding the Examples are Preparations 1 to 4 which describe the production of starting materials. Examples A to L exemplify the preparation of amines of formula II and related intermediates, and Examples 1–32 of compounds of formula I. Example 33 exemplifies pharmaceutical compositions.

PREPARATION 1

(a) 5-(Methylamino)methyl-2-furanmethanol

A mixture of 2-furanmethanol (49 g), methylamine hydrochloride (51.5 g) and 36% formaldehyde solution (50 ml) was stirred at 0°–3° for 3 hr and allowed to stand for 16 hr. Excess sodium carbonate was added and the slurry extracted with ethyl acetate. After removal of solvent the residue was distilled to give 5-(methylamino)methyl-2-furanmethanol (36.2 g) b.p. 111°–113° (0.2 mm).

Similarly prepared from 2-furanmethanol and the corresponding amine hydrochloride were:

(b) 5-[(2-Phenylethyl)amino]methyl-2-furanmethanol. Oil Rf 0.45 (silica/acetone). NMR (CCl4) 7.29, br.s (4H); 6.8 s (2H); 6.40 s (2H); 5.62 s (2H); 4.0 br (2H); 2.87 s (5H).

(c) 5-[(1-Methylethyl)amino]methyl-2-furanmethanol. Oil Rf 0.55 (silica/methanol). Analysis Found C, 63.35; H, 8.78; N, 8.09. $C_9H_{15}NO_2$ requires C, 63.88; H, 8.94; N, 8.28%.

(d) 5-(Ethylmethylamino)methyl-2-furanmethanol. Rf 0.32 (silica/acetone). NMR (CDCl3) 8.93 t (3H); 7.80 s (3H); 7.55 q (2H); 6.50 s (2H); 6.33 br.s (1H); 5.47 s (2H); 3.80 m (2H).

(e) 5-[[2-(Dimethylamino)ethyl]amino]methyl-2-furanmethanol bis maleate salt m.p. 119°–121°.

PREPARATION 2

5-[2-(N,N-dimethylamino)ethyl]-2-furanmethanol

N,N-Dimethyl-2-furanethanamine (9.8 g), 30% aqueous formaldehyde (17.5 g) and glacial acetic acid (18 ml) were heated at 70° for 5 hr. The reaction was cooled, basified with sodium hydroxide and extracted with ether. The organic extracts were distilled to give an oil b.p. 90°–100° (0.5 mm). Found: C, 64.0; H, 8.9; N, 8.0. $C_9H_{15}NO_2$ requires: C, 63.9; H, 8.9; N, 8.2%.

PREPARATION 3

2[1-(4-Bromomethyl)]furan n-Butyl lithium (1.6 M in hexane, 375 ml) was added to a solution of furan (40.8 g) in dry tetrahydrofuran (375 ml) and the mixture was stirred at 40° for 3 hr. 1,4-Dibromobutane (129.6 g) was then added at −30° and the reaction stirred at room temperature for 4 hr. Water was added and the mixture was extracted with ethyl acetate. Distillation of the extract gave a clear colourless liquid b.p. 60°–62°, 0.5 mm Hg.

N,N-Dimethyl-4-(2-furanyl)butanamine

Dimethylamine (56 g) was added to a solution of 2-[1-(4-bromobutyl)]furan (82 g) in toluene (500 ml). The resultant solution was stirred at room temperature for 2 days, and then acidified with hydrochloric acid. The acid layer was separated, washed with ether, basified with sodium hydroxide and extracted with ether. The ethereal extract was distilled to give a clear colourless oil b.p. 55°–58°, 0.8 mm Hg. Hydrochloride salt m.p. 133°–136°. Found: C, 59.01; H, 9.02; H, 6.87. Calc. for $C_{10}H_{17}NO.HCl$: C, 58.96; H, 8.91; N, 6.88%.

5-[4-(Dimethylamino)butyl]-2-furanmethanol (a) n-Butyl lithium (1.6 M in n-hexane, 125 ml) was added to an ice-cooled solution of N,N-dimethyl-4-(2-furanyl)butanamine (33.4 g) in dry tetrahydrofuran (125 ml). The mixture was stirred at room temperature for 4 hr. Paraformaldehyde (6.0 g) was then added and the mixture stirred for a further 1 hr. The reaction was quenched with water and extracted with chloroform. The organic extracts were distilled to give a clear colourless oil b.p. 100°–105°, 0.1 mm Hg, m.p. 26°–28.5°. Found: C, 67.09; H, 10.01; N, 7.06. Calc. for $C_{11}H_{19}NO_2$: C, 66.97; H, 9.71; N, 7.10%.

Similarly prepared was:

(b) 5-[3-(Dimethylamino)propyl]-2-furanmethanol, b.p. 160°/0.08 mm Hg, m.p. ca. 24°. Found: C, 64.66; H, 9.36; N, 7.39. Calc. for $C_{10}H_{17}NO_2.1/5\ H_2O$: C, 64.28; H, 9.39; N, 7.50%.

PREPARATION 4

[5-[4-[N,N-Dimethylamino]butyl]-2-furanyl]methyl ethanoate

A mixture of 5-[4-(dimethylamino)butyl]-2-furanmethanol (4.9 g), acetic anhydride (25 g) and fused and powdered sodium acetate (10 g) in benzene (25 ml) was stirred at room temperature for 24 hr. The reaction was diluted with water (100 ml) and extracted with ethyl acetate. The combined extracts were distilled to afford a clear colourless oil b.p. 100°, 0.5 mm Hg. Found: C, 62.52; H, 9.03; N, 5.95. Calc. for $C_{13}H_{21}NO_3$: C, 65.24, H, 8.85; N, 5.85%.

EXAMPLE A (a)
2-[[[5-(Dimethylamino)methyl-2-furanyl]methyl]thio]ethanamine 5-(Dimethylamino)methyl-2-furanmethanol (15.5 g) was added dropwise to a stirred, ice-cold solution of cysteamine hydrochloride (11.36 g) in concentrated hydrochloric acid (40 ml). After standing at 0° for 18 hr, excess anhydrous sodium carbonate was added and the resultant solid extracted with diethyl ether. Removal of solvent followed by distillation of the residue gave 2-[[[5-(dimethylamino)methyl-2-furanyl]methyl]thio]ethanamine (11.6 g) b.p. 104°–106° (0.1 mm). Picrate salt m.p. 142°–144°.

Similarly prepared from the corresponding furanmethanols and cysteamine hydrochloride were:

(b) 2-[[[5-(Methylamino)methyl-2-furanyl]methyl]thio]ethanamine. Monopicrate salt m.p. 116°–118°.

(c) 2-[[[5-[(1-Methylethyl)amino]methyl-2-furanyl]methyl]thio]ethanamine. Oil Rf 0.4 (silica/methanol:0.880 ammonia 79:1).

(d) 2-[[[5-(Diethylaminomethyl)-2-furanyl]methyl]thio]ethanamine b.p. 134°–135° (1 mm).

(e) 2-[[[5-(1-Piperidinyl)methyl-2-furanyl]methyl]thio]ethanamine. Oil Rf 0.37 (silica/methanol:0.880 ammonia 79:1).

(f) 2-[[[5-(Aminomethyl)-2-furanyl]methyl]thio]ethanamine, dihydrochloride m.p. 222°–224° (dec.).

(g) N-[5-[[[(2-Aminoethyl)thio]methyl]-2-furanyl]methyl]benzene ethanamine. Oil Rf 0.33 (silica/methanol:0.880 ammonia 79:1).

(h) 2-[[[5-[2-(Dimethylamino)ethyl]-2-furanyl]methyl]thio]enthanamine b.p. 150°–155° (0.04 mm).

(i) 2-[[[5-[3-(Dimethylamino)propyl]-2-furanyl]methyl]thio]ethanamine b.p. 150° (0.05 mm).

(j) 2-[[[5-(Ethylmethylamino)methyl-2-furanyl]methyl]-thio]ethanamine Rf 0.34 (silica/methanol:0.880 ammonia 79:1).

(k) 2-[[[5-[(2-Dimethylaminoethyl)amino]methyl-2-furanyl]methyl]thio]ethanamine. Tris maleate salt m.p. 132°–135°.

(l) 2-[[[5-(1-Pyrrolidino)methyl-2-furanyl]methyl]thio]ethanamine. Bis oxalate salt m.p. 136.5°–138.5°.

EXAMPLE B

2-[[[5-[4-(Dimethylamino)butyl]-2-furanyl]methyl]thio]ethanamine

Cysteamine hydrochloride (4.5 g) was added to a cooled solution of potassium-t-butoxide (8.98 g) in dry dimethylformamide (125 ml). The mixture was stirred for 20 min and [5-[4-(dimethylamino)butyl]-2-furanyl]methyl ethanoate (9.6 g) was added. The reaction was heated at 90° for 4 hr, poured onto an ice-water mixture and extracted with chloroform. Distillation of the organic extract gave a yellow oil which after column chromatography on silica, using methanol/0.880 ammonia (9:1) as eluent, and a further distillation afforded a colourless oil b.p. 140°/0.05 mm Hg. Found: C, 60.81; H, 9.86; N, 10.44. Calc. for $C_{13}H_{24}N_2OS$: C, 60.91; H, 9.44; N, 10.93%.

EXAMPLE C

2-[[2-(2-Furanyl)ethyl]thio]ethyl-1H-isoindole-1,3(2H)dione

80% Sodium hydride (0.155 g) was added portionwise to a solution of 2-phthalimido-ethanethiol (1.03 g) in dry dimethylformamide at 0°. After 20 mins a solution of 2-furanethanol, 4-methylbenzenesulphonate (1.33 g) in dry dimethylformamide was added dropwise and the solution stirred overnight at room temperature. The mixture was poured into ice-water and 2-[[2-(2-furanyl)ethyl]thio]ethyl-1H-isoindole-1,3(2H)-dione isolated as a white solid (1.3 g) m.p. 53°–55°.

EXAMPLE D (a)

2-[2-[[)2-Furanyl)methyl]thio]ethyl]-1H-isoindole-1,3(2H)-dione

80% Sodium hydride (1.58 g) was added in portions to a solution of furfuryl mercaptan (6 g) in dry dimethylformamide (50 ml). After 30 mins a solution of 2-bromoethylphthalimide (16.71 g) was added in dry dimethylformamide (65 ml) and the solution heated at 110° for 2 days. After removal of solvents the residue was washed with water and extracted with ethyl acetate. The ethyl acetate extracts were combined, the solvent removed and the residue recrystallised from cyclohexane to give 2-[2-[[(2-furanyl)methyl]thio]ethyl]-1H-isoindole-1,3(2H)-dione m.p. 62°–63° (7.8 g).

Similarly prepared from the ω-bromoalkylphthalimide and furfuryl mercaptan were:

(b) 2-[3-[[(2-Furanyl)methyl]thio]propyl]-1H-isoindole-1,3(2H)-dione, NMR (CDCl$_3$) 7.7–8.3 m (2H); 7.2–7.7 m (2H); 6.29 s (2H); 6.23 t (2H); 3.7 m (2H); 2.7 m (1H); 2.4 m (4H).

(c) 2-[4-[[(2-Furanyl)methyl]thio]butyl]-1H-insoindole-1,3(2H)-dione, NMR (CDCl$_3$) 8–8.5 m (4H); 7.49 t (2H); 6.33 m (4H); 3.7 n (2H); 2.7 m (1H); 2.3 m (4H).

EXAMPLE E (a)

2-[2-[[[5-(Dimethylamino)methyl-2-furanyl]methyl]thio]ethyl]-1H-isoindole-1,3(2H)-dione A mixture of 2-[2-[[(2-furanyl)methyl]thio]ethyl]-1H-isoindole-1,3(2H)-dione (10 g), dimethylammonium chloride (3.1 g) and 36% formaldehyde solution (3 ml) in acetic acid (50 ml) was heated on a steam bath for 9 hr. The solution was cooled and solvent removed in vacuo. The residue was basified with 5 N sodium hydroxide and extracted with ethyl acetate. The organic phase was treated with charcoal, dried and evaporated to give an oil which was purified by column chromatography (silica/ethanol:ethyl acetate 1:1) (5.7 g) Rf 0.4. NMR (CDCl$_3$/DMSO) 7.71 s (6H); 7.22 t (2H); 6.52 s (2H); 6.2 s (2H); 6.1 t (2H); 3.8 m (2H); 2.2 m (4H).

Similarly prepared from 2-[ω-[[(2-furanyl)methyl]thio]alkyl]-1H-isoindole-1,3(2H)-dione, the corresponding amine and formaldehyde were:

(b) 2-[2-[[[5-[(1-Pyrrolidinyl)methyl]-2-furanyl]methyl]thio]ethyl]-1H-isoindole-1,3(2H)-dione. NMR (CDCl$_3$) 8–8.4 m (4H); 7–7.6 m (6H); 6–6.5 m (6H); 3.7–4.0 m (2H); 2–2.4 m (4H).

(c) 2-[3-[[[5-(Dimethylamino)methyl-2-furanyl]methyl]thio]propyl]-1H-isoindole- 1,3(2H)-dione. Rf 0.45 (silica/methanol).

(d) 2-[4-[[[5-(Dimethylamino)methyl-2-furanyl]methyl]thio]butyl]-1H-isoindole-1,3(2H)-dione. Rf 0.26 (silica/methanol). NMR (CDCl$_3$) 8.85 m (4H); 7.7 s (6H); 7.42 t (2H); 6.52 s (2H); 6.29 m (4H); 3.9 m (2H); 2–2.4 m (4H).

(e) 2-[2-[[[5-[(4-Methyl-1-piperazinyl)methyl]-2-furanyl]methyl]thio]ethyl]-1H-isoindole-1,3(2H)-dione. NMR (CDCl$_3$) 7.75 s (3H); 7.52 s (8H); 7–7.5 m (2H); 6.5 s (2H); 6–6.3 m (4H); 3.85 m (2H); 2–2.4 m (4H).

(f) 2-[2-[[[5-[(4-Morpholinyl)methyl]-2-furanyl]methyl]thio]ethyl]-1H-isoindole-1,3(2H)-dione. NMR (CDCl$_3$) 7.54 m (4H); 7.24 m (2H); 6.50 s (2H); 6.22 m (8H); 3.8 m (2H); 2.0–2.4 m (4H).

EXAMPLE F

2-[2-[[2-[5-(Dimethylamino)methyl-2-furanyl]ethyl]thio]ethyl]-1H-isoindole-1,3(2H)-dione 2-[[2-(2-Furanyl)ethyl]thio]ethyl-1H-isoindole-1,3(2H)-dione (0.5 g), dimethylamine hydrochloride (0.27 g) and paraformaldehyde (0.102 g) were heated together under reflux in ethanol. After 5 hr further dimethylamine hydrochloride (0.27 g) and paraformaldehyde (0.102 g) were added and the heating continued for a further 16 hr. Solvent was removed, the residue basified and extracted with ethyl acetate to give an oil which after column chromatography (silica/methanol) gave 2-[2-[[2-[5-(dimethylamino)methyl-2-furaryl]ethyl]thio]ethyl]-1H-isoindole-1,3(2H)dione as a pale oil (0.43 g). Analysis Found: C, 61.48; H, 6.13; N, 7.63; $C_{19}H_{22}N_2O_3S.3/4 H_2O$ requires: C, 61.35; H, 6.37; N, 7.53%.

EXAMPLE G

2-[[5-(Dimethylamino)methyl-2-furanyl]methoxy]ethanamine

Route (i)

To a solution of 5-(dimethylamino)methyl-2-furanmethanol (6.2 g) and ethylene imine (2.82 g) in dry tetrahydrofuran was added a solution of methanesulphonic acid (11.6 g) in tetrahydrofuran (40 ml). The solution was evaporated and the oily residue heated at 98°–100° for 10 mins. After 18 hr, 5 N sodium hydroxide (60 ml) was added and the solution evaporated to dryness. Anhydrous sodium sulphate and ethyl acetate (150 ml) were added and after 2 hr the suspension was filtered, treated with decolourising charcoal and evaporated. The resulting oil was chromatographed on silica, firstly with methanol-ammonia 0.88 79:1, and the eluate discarded, and secondly with methanol-ammonia 0.88 19:1. This eluate was evaporated to give an oil from which the bisoxalate salt of 2-[[5-(dimethylamino)methyl-2-furanyl]methoxy]ethanamine (from ethanol) 0.2 g, m.p. 125°–128°, was obtained.

Route (ii)

A solution of 2-chloroethylamine hydrochloride (6.25 g) in dry dimethylformamide was added dropwise to a stirred, cooled solution of potassium tert-butoxide (8.96 g) and 5-(dimethylamino)methyl-2-furanmethanol (12.4 g) in the same solvent. After 2 hr solvent was removed, the residue basified and extracted with ethyl acetate. The residue after removal of solvent was treated in ethanol with ethanolic oxalic acid. The crystalline salt was recrystallised from ethanol to give 2-[[5-(dimethylamino)methyl-2-furanyl]methoxy]ethanamine, bis oxalate, m.p. 130°–133° (3.05 g).

Similarly prepared by route (ii) was:
(b) 2-[[5-(Methylamino)methyl-2-furan]methoxy]ethanamine, bis oxalate m.p. 162°–164°.

EXAMPLE H (a) 2-[4-(2-Furanyl)butyl]-1H-isoindole-1,3(2H)-dione

2[1-(4-bromobutyl)]furan (406 mg) and potassium phthalimide (370 mg) were stirred together at room temperature in dry dimethylformamide overnight. The solution was poured into ice-water and the resulting white solid filtered, dried and recrystallised from chloroform/petroleum ether (b.p. 60°–80°) to give 2-[4-(2-Furanyl)butyl]-1H-isoindole-1,3(2H)-dione as white microcrystals (430 mg) m.p. 61°–63°.

In a similar manner was prepared:
(b) 2-[5-(2-Furanyl)pentyl]-1H-isoindole-1,3(2H)-dione, m.p. 54°–56°.

EXAMPLE I (a)
2-[4-[5-(Dimethylamino)methyl-2-furanyl]butyl]-1H-isoindole-1,3(2H)-dione 2-[4-(2-Furanyl)butyl]-1H-isoindole-1,3(2H)-dione (5.38 g), paraformaldehyde (1.2 g) and dimethylamine hydrochloride (3.26 g) were refluxed in absolute ethanol (100 ml). After 6 hr further paraformaldehyde (0.6 g) and dimethylamine hydrochloride (1.6 g) were added and heating continued for a further 20 hr. The solvent was removed, the residue made strongly basic with 5 N sodium hydroxide, extracted with ethyl acetate and the organic layer evaporated. The crude product was purified by column chromatography to give an amber oil (3.25 g) Rf 0.4 silica/methanol. NMR (CDCl$_3$) 8–8.6 m (4H); 7.75 s (6H); 7.3 m (2H); 6.55 s (2H); 6.3 m (2H); 4.0 m (2H); 1.9–2.4 m (4H).

In a similar manner was prepared:
(b) 2-[5-[5-(Dimethylamino)methyl-2-furanyl]pentyl]-1H-isoindole-1,3(2H)-dione. TLC Rf 0.4 silica/methanol. NMR 8.0–8.8 m (6H); 7.70 m (6H); 7.37 t (2H); 6.52 s (2H); 6.30 t (2H); 4.0 m (2H); 2.2 m (4H).

EXAMPLE J 5-(Dimethylamino)methyl-2-furanpropanamine

Furanpropionitrile (1.21 g), dimethylamine hydrochloride (1.62 g) and paraformaldehyde (0.7 g) in ethanol (20 ml) were heated under reflux for 24 hr. Solvents were removed, the residue basified to pH 12 and extracted with ethyl acetate. After removal of solvents the residual oil was purified by column chromatography (silica/methanol) and 5-(dimethylamino)methyl-2-furanpropionitrile isolated (0.6 g) Rf 0.55 (silica/methanol).

The nitrile (6.0 g) in dry ether (40 ml) was added dropwise with stirring to lithium aluminium hydride (2.0 g) in ether at 0°. Addition of water, followed by removal of solvents, gave, after column chromatography, 5-(dimethylamino)methyl-2-furanpropanamine as a pale oil (3.33 g). NMR (CDCl$_3$) 8.2 m (2H); 7.6 br (2H); 7.75 s (6H); 7.30 m (4H); 6.60 s (2H); 4.0 m (2H).

EXAMPLE K

2-[3-[[[5-(Dimethylamino)methyl-2-furanyl]thio]-propyl]]-1H-isoindole-1,3(2H)-dione Sulphur (1.9 g) was added in portions to a solution of the lithio derivative of N,N-dimethylfuranmethaneamine (7.5 g) at −40°. The mixture was stirred at −10° for 20 mins and 2-(3-bromopropyl)1H-isoindole-1,3(2H)-dione (16 g) added. The mixture was left at 0° overnight, solvent removed in vacuo and the residue in ethyl acetate filtered and extracted with 2N sulphuric acid. The aqueous layer was basified, re-extracted with ethyl acetate and the organic phase dried. Removal of the solvent gave a crystalline solid, which recrystallised from ethanol (charcoal) to give 2-[3-[[[5-(dimethylamino)methyl-2-furanyl]thio]propyl]]-1H-isoindole-1,3(2H)-dione (7.59 g) m.p. 64°–65°.

EXAMPLE L (a) 4-[5-(Dimethylamino)methyl-2-furanyl]butanamine

2-[[4-(5-Dimethylamino)methyl-2-furanyl]butyl]-1H-isoindole-1,3(2H)-dione (2.9 g) and hydrazine hydrate (0.55 ml) were refluxed in ethanol for 6 hr. Solvent was removed and the crystalline residue dissolved in 5N sodium hydroxide solution. This was extracted with ethyl acetate which on removal of solvent gave the product as a mobile yellow oil (1.68 g). TLC Silica/methanol single spot Rf 0.15. NMR (CDCl$_3$) 8.0–8.8 m (4H); 7.7 s (6H); 7.6 br (2H); 7.3 m (4H); 6.58 s (2H); 4.0 m (2H).

In a similar manner were prepared from the corresponding phthalimide:
(b) 5-[5-(Dimethylamino)methyl-2-furanyl]pentanamine. NMR (CDCl$_3$) 8.0–8.8 m (6H); 7.75 s (6H); 7.0–7.6 m (4H); 6.60 s (2H); 4.0 m (2H).
(c) 5-[[(3-Aminopropyl)thio]methyl]-N,N-dimethylfuran-2-methanamine. NMR (CDCl$_3$) 8–8.5 m (2H); 7.75 s (6H); 7.42 t (2H); 7.25 m (2H); 6.58 s (2H); 6.3 s (2H); 3.88 s (2H).

EXAMPLE 1

(a)
N-[2-[[[5-(Dimethylamino)methyl-2-furanyl]methyl]thio]ethyl]-N'-methylthiourea 2-[2-[[[5-(Dimethylamino)methyl-2-furanyl]methyl]thio]ethyl]-1H-isoindole-1,3(2H)-dione (5.3 g) and hydrazine hydrate (0.85 g) were refluxed in ethanol for 30 hr. Evaporation of the solvent gave the phthalhydrazide salt of 2-[[[5-(dimethylamino)methyl-2-furanyl]methyl]thio]ethanamine.

This salt (1 g) was suspended in acetonitrile and methylisothiocyanate (0.21 g) added. The suspension was stirred at room temperature for 5 hr and at 60° for 2 hr, filtered and evaporated to give an oil which was purified by column chromatography (silica/methanol). N-[2-[[[5-(Dimethylamino)methyl-2-furanyl]methyl]thio]ethyl]-N'-methylthiourea was isolated as a pale oil (0.3 g). Analysis Found: C, 49.68; H, 7.52; 14.22; $C_{12}H_{21}N_3OS_2$ requires: C, 50.14; H, 7.37; N, 14.62%.

Similarly prepared were:
(b) N-Methyl-N'-[2-[[[5-(1-pyrrolidinyl)methyl-2-furanyl]methyl]thio]ethyl]thiourea. Analysis Found: C, 52.33; H, 7.12; N, 13.17. $C_{14}H_{23}N_3OS_2.\tfrac{1}{2}H_2O$ requires: C, 52.14; H, 7.50; N, 13.03%.
(c) N-[4-[[[5-(Dimethylamino)methyl-2-furanyl]methyl]thio]butyl]-N'-methylthiourea. Analysis Found: C, 51.69; H, 8.53, N, 12.83; $C_{14}H_{25}N_3OS_2$ requires: C, 51.82; H, 8.08; N, 12.95%.
(d) N-[3-[[5-(Dimethylamino)methyl-2-furanyl]thio]propyl]-N'-methylthiourea. Analysis Found: C, 49.71; H, 7.33; N, 14.35. $C_{12}N_{21}N_3OS_2$ requires: C, 50.10; H, 7.50; N, 14.62%.
(e) N-Methyl-N'-[2-[[5-(4-morpholinyl)methyl]-2-furanyl]methyl]thio]ethyl]thiourea. Analysis Found: C, 51.26; H, 7.08; N, 12.51. $C_{14}H;hd 23N_3O_2S_2$ requires: C, 51.03; H, 7.04; N, 12.75%.
(f) N-Methyl-N'-[2-[[[5-[(4-methyl-piperazinyl)methyl]-2-furanyl]methyl]thio]ethyl]thiourea. Analysis Found: C, 50.93; H, 7.74; N, 15.82. $C_{15}H_{26}N_4OS_2$ requires: C, 51.25; H, 8.03; N, 15.94%.
(g) N-[2-[[2-[5-(Dimethylamino)methyl-2-furanyl]ethyl]thio]ethyl]-N'-methylthiourea. Analysis Found: C, 50.19; H, 7.20; N, 13.18. $C_{13}H_{23}N_3O_2O.\tfrac{1}{2}H_2O$ requires: C, 50.32; H, 7.74; N, 13.54%.

EXAMPLE 2

(a)

N-[5-[5-(Dimethylamino)methyl-2-furanyl]pentyl]-N'-methylthiourea

5-[5-(Dimethylamino)methyl-2-furanyl]pentanamine (0.5 g) and methylisothiocyanate (0.25 g) were stirred in acetonitrile at room temperature for 24 hr. Solvent was removed and the product purified by column chromatography (silica/methanol) to give after trituration with ether N-[5-[5-(dimethylamino)methyl-2-furanyl]pentyl]-N'-methylthiourea as off-white crystals m.p. 66°-69°.

Similarly prepared from the corresponding amine and methylisothiocyanate were:
(b) N-[3-[[[5-(Dimethylamino)methyl-2-furanyl]methyl]thio]propyl]-N'-methylthiourea. Analysis Found: C, 51.38; H, 7.93; N, 13.41. $C_{13}H_{23}N_2OS_2$ requires: C, 51.79; H, 7.69; N, 13.94%.
(c) N-[4-[5-(Dimethylamino)methyl-2-furanyl]butyl]-N'-methylthiourea. NMR $\tau(CDCl_3)$ 8-8.6 m (4H); 7.72 s (6H); 7.35 t (2H); 6.98 d (3H); 6.2-6.8 m (4H); 4.0 d (2H); 3-3.8 m (2H).
(d) N-[2-[[5-(Dimethylamino)methyl-2-furanyl]methoxy]ethyl]-N'-methylthiourea. Analysis Found: C, 51.91; H, 8.14; N, 14.98. $C_{12}H_{21}N_3O_2S.\tfrac{1}{2}H_2O$ requires: C, 51.40; H, 7.91; N, 14.99%.

EXAMPLE 3

(a)

N-[2-[[[5-(Dimethylamino)methyl-2-furanyl]methyl]thio]ethyl]-N'-(2-methoxyethyl)thiourea 1-(Isothiocyanato)-2-methoxyethane (1.17 g) and 2-[[[5-(dimethylamino)methyl-2-furanyl]methyl]thio]ethanamine (2.14 g) in acetonitrile were stood overnight. Solvent was removed and the residual oil chromatographed (silica/methanol) to give N-[2-[[[5-(dimethylamino)methyl-2-furanyl]methyl]thio]ethyl]-N'-(2-methoxyethyl)thiourea as a pale oil Rf 0.45. Analysis Found: C, 50.64; H, 7.51; N, 12.58. $C_{14}H_{25}N_3O_2S_2$ requires: C, 50.75; H, 7.55; N, 12.69%.

Similarly prepared from the corresponding isothiocyanate and 2-[[[5-(dimethylamino)methyl-2-furanyl]methyl]thio]ethanamine were:
(b) N-[2-[[[5-(Dimethylamino)methyl-2-furanyl]methyl]thio]ethyl]-N'-(2-propenyl)thiourea. Found: C, 52.68; H, 7.58; N, 13.16. $C_{14}H_{23}N_3OS_2.\tfrac{1}{2}H_2O$ requires: C, 52.14; H, 7.50; N, 13.03%.
(c) N-[2-[[[5-(Dimethylamino)methyl-2-furanyl]methyl]thio]ethyl]-N-(1-methylethyl)thiourea. Analysis Found: C, 51.84; H, 7.88; N, 13.00. $C_{14}H_{25}N_3OS_2.\tfrac{1}{2}H_2O$ requires: C, 51.90; H, 8.09; N, 12.97%.

EXAMPLE 4

N-[2-[[[5-(Methylamino)methyl-2-furanyl]methyl]thio]ethyl]-N'-methylurea

To a stirred solution of 2-[[[5-(methylamino)methyl-2-furanyl]methyl]thio]ethanamine (1.5 g) in acetonitrile (24 ml) was added dropwise a solution of methylisocyanate (0.45 g) in acetonitrile (15 ml). After 30 mins the solution was evaporated to dryness to give an oil which was column chromatographed firstly on silica/methanol: 0.88 ammonia 79:1 then alumina/methanol to give an oil consisting of N-[2-[[[5-(methylamino)methyl-2-furanyl]methyl]thio]ethyl]-N'-methylurea (0.25 g). Analysis Found: C, 51.00; H, 7.38; N, 15.91. $C_{11}N_{19}N_3O_2S$ requires: C, 51.33; H, 7.44; N, 16.33%.

EXAMPLE 5

(a)

N-[2-[[[5-(Dimethylamino)methyl-2-furanyl]methyl]thio]ethyl]-N'-methylurea

Methylisocyanate (0.33 g) was added to a suspension of 2-[[[5-(dimethylamino)methyl-2-furanyl]methyl]thio]ethanamine, phthalhydrazine complex (2 g) in acetonitrile (50 ml). After 2 hr the solution was filtered and the filtrate evaporated to give an oil which was purified by column chromatography (silica/methanol) to give N-[2-[[[5-(dimethylamino)methyl-2-furanyl]methyl]thio]ethyl]-N'-methylurea. Analysis Found: C, 52.38; H, 7.61; N, 15.25. $C_{12}H_{21}N_3O_2S.\tfrac{1}{2}H_2O$ requires: C, 52.24; H, 7.76; N, 15.32%.

Similarly prepared was:
(b) N-Methyl-N'-[2-[[[5-(1-pyrrolidinyl)methyl-2-furanyl]methyl]thio]ethyl]urea. Analysis Found: C, 54.70; H, 7.33; N, 14.07. $C_{14}H_{23}N_3O_2S.\tfrac{1}{2}H_2O$ requires: C, 54.87; H, 7.89; N, 13.71%.

EXAMPLE 6

(a) N-[2-[[[5-(Dimethylamino)methyl-2-furanyl]methyl]thio]ethyl]-N'-(1-methylethyl)urea 2-[[[5-(Dimethylamino)methyl-2-furanyl]methyl]thio]ethanamine (2.14 g) and isopropylisocyanate (0.89 g) were dissolved in acetonitrile and allowed to stand overnight. Solvents were removed and the residue recrystallised from methanol:ether to give N-[2-[[[5-(dimethylamino)methyl-2-furanyl]methyl]thio]ethyl]-N'-(1-methylethyl)urea as crystals m.p. 65°-67° (2.8 g).

Similarly prepared were:

(b) N-[3-[[[5-(Dimethylamino)methyl-2-furanyl]methyl]thio]propyl]-N'-methylurea m.p. 69°-69.5°.

EXAMPLE 7

N-[2-[[[5-(Dimethylamino)methyl-2-furanyl]methyl]thio]ethyl]urea

A solution of 2-[[[5-(dimethylamino)methyl-2-furanyl]methyl]thio]ethanamine dihydrochloride (2.8 g) and potassium cyanate (3.75 g) in water (50 ml) was heated on a steam bath for 8 hr. Excess solid sodium carbonate was added and organic material continually extracted with diethyl ether. The extracts were evaporated and the residue after column chromatography yielded N-[2-[[[5-(dimethylamino)methyl-2-furanyl]methyl]thio]ethyl]urea as a waxy solid (1.28 g). Analysis Found: C, 48.22; H, 7.50; N, 15.61. $C_{11}H_{19}N_3O_2S.H_2O$ requires: C, 48.00; H, 7.63; N, 15.27%.

EXAMPLE 8

N-[2-[[[5-(Dimethylamino)methyl-2-furanyl]methyl]thio]ethyl]-N'-nitroguanidine

A solution of 2-[[[5-dimethylamino)methyl-2-furanyl]methyl]thio]ethanamine (2.14 g) and S-methyl-N-nitroisothiourea (1.5 g) in ethanol (10 ml) was heated to 40° for 5 mins. The resulting precipitate was filtered and recrystallised from ethyl acetate and petroleum ether b.p. 80°-100° to give N-[2-[[[5-(dimethylamino)-methyl-2-furanyl]methyl]thio]ethyl]-N'-nitroguanidine m.p. 103°-104°.

EXAMPLE 9

(a) N-Cyano-N'-[2-[[[5-(methylamino)methyl-2-furanyl]methyl]thio]ethyl]-N"-methylguanidine A mixture of 2-[[[5-(methylamino)methyl-2-furanyl]methyl]thio]ethanamine (2.0 g) and N-cyano-N'-methylcarbamimidothioic acid, methyl ester (1.25 g) was heated on a steam bath for 6.5 hr. Vacuum was applied at regular intervals to remove methanethiol. The crude product was purified by column chromatography Rf 0.65 (silica/methanol:ammonia 79:1) to give N-cyano-N'-[2-[[[5-(methylamino)methyl-2-furanyl]methyl]thio]ethyl]-N"-methylguanidine (1.05 g) m.p. 81°-85°.

In a similar manner were prepared from the corresponding amine and N-cyano-N'-methylcarbamimidothioic acid, methyl ester:

(b) N-Cyano-N'-[2-[[[5-(1-methylethyl)amino]methyl-2-furanyl]methyl]thio]ethyl]-N"-methylguanidine.
Analysis Found: C, 54.73; H, 7.82; N, 22.31. $C_{14}H_{23}N_5OS$ requires: C, 54.34; H, 7.49; N, 22.64%.

(c) N-Cyano-N'-[2-[[[5-(diethylamino)methyl-2-furanyl]methyl]thio]ethyl]-N"-methylguanidine.
Analysis Found: C, 53.54; H, 7.82; N, 20.65. $C_{15}H_{25}N_5OS.\frac{1}{2}H_2O$ requires: C, 53.46; H, 7.70; N, 20.78%.

(d) N-Cyano-N'-[2-[[[5-(1-pyrrolidinyl)methyl-2-furanyl]methyl]thio]ethyl]-N"-methylguanidine.
Analysis Found: C, 53.97; H, 6.87; N, 21.06. $C_{15}H_{23}N_5OS.\frac{1}{2}H_2O$ requires: C, 53.79; H, 7.37; N, 20.91%.

(e) N-Cyano-N'-[3-[[[5-(dimethylamino)methyl-2-furanyl]methyl]thio]propyl]-N"-methylguanidine.
Analysis Found: C, 52.86; H, 7.49; N, 20.64; $C_{14}H_{23}N_5OS.\frac{1}{2}H_2O$ requires: C, 52.80; H, 7.59; N, 21.20%.

EXAMPLE 10

N-Cyano-N'-[2-[[[5-(dimethylamino)methyl-2-furanyl]methyl]thio]ethyl]-N"-methylguanidine To a stirred suspension of potassium carbonate (20.7 g) in a solution of 2-[[[5-(dimethylamino)methyl-2-furanyl]methyl]thio]ethanamine (10.7 g) and N-cyano-N'-methylcarbamimidothioic acid methyl ester (7.1 g) in acetonitrile (107 ml) at 70° was added a solution of silver nitrate (9.35 g) in acetonitrile (20 ml) during 1 hr. The mixture was stirred for 16 hr, the solid filtered and the filtrate evaporated to dryness. The residue was dissolved in ethyl acetate (250 ml). A portion of this (10.5 ml) was washed with water (6 ml), the ethyl acetate layer evaporated to give a solid which was crystallised from isoproplyacetate (1.75 ml) giving N"-cyano-N-[2-[[[5-(dimethylaminomethyl)-2-furanyl]methyl]thio]ethyl]-N'-methylguanidine (0.35 g) m.p. 79°-81.5°.

To a further portion (225 ml) was added a solution of sebacic acid (9.09 g) in ethanol (30 ml), the filtered solution giving the sebacate salt (13.74 g) m.p. 92.5°-94°. Analysis FOund: C, 54.91; H, 7.94; N, 14.02. $C_{13}H_{21}N_5OS.C_{10}H_{18}O_4$ requires: C, 55.51; H, 7.90; N, 14.07%.

EXAMPLE 11

N-Cyano-N'-(2-methoxyethyl)carbamimidothioic acid, methyl ester

Powered cyanamide (4.2 g) was added to a stirred solution of sodium (2.3 g) in absolute ethanol. After 30 mins a solution of methoxyethylisothiocyanate (11.7 g) in absolute ethanol was added to the cooled solution. After a further hour at room temperature dimethyl sulphate (12.66 g) was added over 30 mins and the mixture stirred overnight. The solvent was removed and remaining solid washed well with water to give N-cyano-N'-2(methoxyethyl)carbamimidothioic acid, methyl ester as a white crystalline solid (12.37 g) m.p. 94.5°-95.5°.

Similarly prepared was:

N-Cyano-N'-(2-propenyl)carbamimidothioic acid, methyl ester, m.p. 109°-110°.

(a) N-Cyano-N'-[2-[[[5-(dimethylamino)methyl-2-furanyl]methyl]thio]ethyl]-N"-(2-methoxyethyl)-guanidine A mixture of 2-[[[5-(dimethylamino)methyl-2-furanyl]methyl]thio]ethanamine (2.14 g) and N-cyano-N'-(2-methoxyethyl)carbamimidothioic acid, methyl ester (1.73 g) was heated on a steam bath for 6.5 hr. Vacuum was applied occasionally to remove methanethiol. The crude product was purified by chromatography (silica gel/methanol) to give N-cyano-N'-[2-[[[5-(dimethylamino)methyl-2-furanyl]methyl]thio]ethyl]-N"-(2-methoxyethyl)guanidine (1.4 g). Analysis Found:

C, 50.51; H, 7.20; N, 19.41, C₁₅H₂₅N₅O₂S.H₂O requires: C, 50.42; H, 7.50; N, 19.60%.

In a similar manner were prepared from 2-[[[5-(dimethylamino)-methyl-2-furanyl]methyl]thio]ethanamine and the corresponding N-alkyl-N'-cyanocarbamimido-thioic acid, methyl ester:

(b) N-Cyano-N'-[2-[[[5-(dimethylamino)methyl-2-furanyl]methyl]thio]ethyl]-N''-(2-propenyl)guanidine. Analysis Found: C, 53.33; H, 7.01; N, 20.70. C₁₅H₂₃N₅OS.H₂O requires: C, 53.09; H, 7.37; N, 20.64%.

(c) N-Cyano-N'-[2-[[[5-(dimethylamino)methyl-2-furanyl]methyl]thio]ethyl]-N''-(1-methylethyl)guanidine. Analysis Found: C, 52.97; H, 7.70; N, 20.57. C₁₅H₂₅N₅OS.H₂O requires: C, 52.78; H, 7.91; N, 20.52%.

EXAMPLE 12

(a) N-[2-[[[5-(Dimethylamino)methyl-2-furanyl]methyl]thio]ethyl]-N'-methylguanidine A mixture of 2-[[[5-(dimethylamino)methyl-2-furanyl]methyl]thio]ethanamine (2.14 g) and N,S-dimethylisothiouronium iodide was heated on a steam bath for 3 hr. The residue in methanol was eluted from an Amberlyst A26 ion exchange resin to give N-[2-[[[5-(dimethylamino)methyl-2-furanyl]methyl]thio]ethyl]-N'-methylguanidine as an amber oil (1.5 g). Analysis Found: C, 50.92; H, 8.23; N, 19.90. C₁₂H₂₂N₄OS.¾H₂O requires: C, 50.76; H, 8.34; N, 19.74%.

Similarly prepared were:

(b) N-[2-[[[5-(Dimethylamino)methyl-2-furanyl]methyl]thio]ethyl]-N',N''-dimethylguanidine. NMR (CDCl₃) 7.75 s (6H); 6.8–7.3 m (8H); 6.5 m (4H); 6.22 s (2H); 3.80 m (2H); 2.0–3.5 br (2H).

EXAMPLE 13

N-Methyl-1-methylthio-2-nitroethanamine

A solution of methylamine in ethanol/ethylenedichloride (112.5 ml of 33% ethanolic methylamine in 0.8 liters of ethylene dichloride; 0.94 mole) was added over 5½ hr at 70° to a stirred solution of 1,1-bismethylthio-2-nitroethene (99.0 g, 0.6 mole) in ethylene dichloride (1.5 liters). The solution was heated to boiling and 0.7 liters of solvent were distilled off. The cooled solution was washed with 2N hydrochloric acid (0.25 liters), then with brine (0.25 liters). The solvent was removed and the residue crystallised from isopropyl acetate (0.5 liters), treating the hot solution with charcoal (10.0 g). The product (35.0 g) formed yellow prisms, m.p. 114°.

N-[2-[[[5-(Methylamino)methyl-2-furanyl]methyl]thio]ethyl]-N'-methyl-2-nitro-1,1-ethenediamine hydrochloride A solution of 2-[[[5-(methylamino)methyl-2-furanyl]methyl]thio]ethanamine (10 g, 0.05 mole) and N-methyl-1-methylthio-2-nitroetheneamine (7.4 g) in water (25 ml) was stirred at 50° for 2 hr. Acetone (350 ml) was added and the solvent was removed by distillation at atmospheric pressure until 275 ml of distillate had been collected. Ethanolic hydrogen chloride (2M; 27.5 ml) was added to the residue and the solution was stirred overnight at room temperature. The product (11.0 g) m.p. 161°, was collected and recrystallised from ethanol as a colourless microcrystalline solid (10.1 g) m.p. 162°. Analysis Found: C, 42.6; H, 6.3; N, 16.4. C₁₂H₂₀N₄O₃S.HCl requires: C, 42.8; H, 6.2; N, 16.6%.

EXAMPLE 14

(a) N-[2-[[[5-(Methylamino)methyl-2-furanyl]methyl]thio]ethyl]-N'-methyl-2-nitro-1,1-ethenediamine A mixture of 2-[[[5-(methylamino)methyl-2-furanyl]methyl]thio]ethanamine (0.9 g) and N-methyl-1-methylthio-2-nitro-etheneamine was heated at 100°–120° for 30 mins under water pump pressure. The residue was purified by column chromatography (silica/methanol: 0.88 ammonia) to give N-[2-[[[5-(methylamino)methyl-2-furanyl]methyl]thio]ethyl]-N'-methyl-2-nitro-1,1-ethenediamine which was crystallised from acetonitrile m.p. 106°–108° (0.65 g).

In a similar manner were prepared:

(b) N-[2-[[[5-[(1-Methylethyl)amino]methyl-2-furanyl]methyl]thio]ethyl]-N'-methyl-2-nitro-1,1-ethenediamine. Analysis Found: C, 49.75; H, 7.21; N, 16.36. C₁₄H₂₄N₄O₃S.½H₂O requires: C, 49.83; H, 7.47; N, 16.60%.

(c) N-Methyl-2-nitro-N'-[2-[[[5-[(2-phenylethyl)amino]methyl-2-furanyl]methyl]thio]ethyl]-1,1-ethenediamine. Analysis Found: C, 57.19; H, 6.53; N, 13.83. C₁₉H₂₆N₄O₃S.½H₂O requires: C, 57.12; H, 6.81; N, 14.02%.

(d) N-Methyl-2-nitro-N'-[2-[[[5-[(1-piperidinyl)methyl]-2-furanyl]methyl]thio]ethyl]-1,1-ethenediamine. Analysis Found: C, 53.36; H, 7.51; N, 14.23. C₁₆H₂₆N₄O₃S.½H₂O requires: C, 53.33; H, 7.44; N, 15.61%.

(e) N-[2-[[[5-[2-[Dimethylamino]ethyl]-2-furanyl]methyl]thio]ethyl]-N'-methyl-2-nitro-1,1-ethenediamine, m.p. 95.5°–96°.

(f) N-[2-[[[5-[3-[Dimethylamino]propyl]-2-furanyl]methyl]thio]ethyl]-N'-methyl-2-nitro-1,1-ethenediamine. NMR τ (CDCl₃), 8.1–7.1 m (6H); 7.65 s (6H); 7.1 s (3H); 6.5 m (2H); 6.28 s (2H); 4.0 m (2H); 3.38 s (1H).

(g) N-[2-[[[5-[4-[Dimethylamino]butyl]-2-furanyl]methyl]thio]ethyl]-N-methyl-2-nitro-1,1-ethenediamine. Waxy solid analysis found: C, 53.90; H, 7.95; N, 15.64. C₁₆H₂₈N₄O₃S requires: C, 53.91; H, 7.92; N, 15.72%.

(h) N-[2-[[[5-(Ethylmethylamino)methyl-2-furanyl]methyl]thio]ethyl]-N'-methyl-2-nitro-1,1-ethenediamine. NMR τ (CDCL₃) 8.90 t (3H); 7.76 s (3H); 6.8–7.5 m (7H); 6.5 br (2H); 6.42 s (2H); 6.25 s (2H); 3.77 s (2H); 3.35 s (1H).

(i) N-[2-[[[5-[[2-(dimethylamino)ethyl]amino]methyl-2-furanyl]methyl]thio]ethyl]-N'-methyl-2-nitro-1,1-ethenediamine. NMR τ (CDCl₃) 7.79 s (6H); 7–7.6 m (10H); 6.6 m (2H); 6.26 s (2H); 6.22 s (2H); 3.85 m (2H); 3.37 s (1H); 2–3.2 br (1H); 0.8–0.2 br (1H).

(j) N-[2-[5-(Dimethylamino)methyl-2-furanylmethoxy]ethyl]-N'-methyl-2-nitro-1,1-ethenediamine, m.p. 110°–112°.

EXAMPLE 15

N-[2-[[[5-Dimethylamino)methyl-2-furanyl]methyl]thio]ethyl]-N'-methyl-2-nitro-1,1-ethenediamine N-Methyl-1-(methylthio)-2-nitroetheneamine (230 g) in water (400 ml) was stirred and heated at 45°–50°. 2-[[[5-(Dimethylamino)methyl-2-furanyl]methyl]thio]ethanamine (321 g) was added dropwise over 4 hr and the resultant solution stirred for a further 3½ hour. The solution was then heated at reflux for ½ hr, cooled to 70° and 4-methylpentan-2-one (2 liters) added. The water was removed by azeotropic distillation under reduced pressure (260 torr) and the resultant solution treated with charcoal (10 g) at 50°. The solution was filtered and cooled to 10°. N-[2-[[[5-(dimethylamino)methyl-2-furanyl]methyl]thio]ethyl]-N'-methyl-2-nitro-1,1-ethenediamine (380 g) was filtered off and dried m.p. 69°–70°.

EXAMPLE 16

N-Methyl-2-nitro-N'-[2-[[[5-[(1-pyrrolidinyl)methyl]-2-furanyl]methyl]thio]ethyl]-1,1-ethenediamine A mixture of 2-[[[5-(1-pyrrolidino)methyl-2-furanyl]methyl]thio]ethanamine bis oxalate salt (2.1 g), potassium hydroxide (1.12 g) and N-methyl-(1-methylthio)-2-nitroethenamine (0.9 g) in water (9 ml) was stirred at room temperature for 18 hours. The water was removed by evaporation under reduced pressure and the residue extracted with ethyl acetate in the presence of excess anhydrous sodium carbonate. Evaporation of the solvent gave a residue which was crystallised from isopropyl acetate as a white crystalline solid (0.9 g) m.p. 79°–82°. Analysis Found: C, 52.78; H, 7.05; N, 16.57. $C_{15}H_{24}N_4O_3S$ requires: C, 52.92; H, 7.11; N, 16.46%.

EXAMPLE 17

N-[2-[[[5-(Methylamino)methyl-2-furanyl]methyl]thio]ethyl]N'-methylurea

To a stirred solution of N-[2-mercaptoethyl]-N'-methylurea (2.0 g) in concentrated hydrochloric acid at 0° was added dropwise a solution of 5-(methylamino)-methyl-2-furanmethanol (2.0 g) in water (3 ml). After 24 hr, ethyl acetate (100 ml) and excess anhydrous sodium carbonate were added. The suspension was filtered, the filtrate evaporated to dryness and the oily residue column chromatographed (silica/methanol:0.88 ammonia 79:1). The relevant eluate was evaporated to dryness to give an oil identical to product of Example 4 (0.42 g).

EXAMPLE 18

N-Cyano-N'-[2-[[[5-(dimethylamino)methyl-2-furanyl]methyl]thio]ethyl]-N"-methylguanidine To a stirred solution of N-cyano-N'-(2-mercaptoethyl)-N"-methylguanidine (1 g) in concentrated hydrochloric acid at 0° was added 5-(dimethylamino)-2-furanmethanol (0.98 g) dropwise during 10 mins. After 3 hr, at room temperature, the solution was neutralized with excess anhydrous sodium carbonate and the resultant solid extracted with ethyl acetate. Evaporation of the solvent gave an oil, which after column chromatography yielded a product identical with the compound of Example 10.

EXAMPLE 19

N-[2-[[5-(Aminomethyl)-2-furanylmethyl]thio]ethyl]-N"-cyano-N'-methylguanidine 2-(5-Chloromethyl-2-furanylmethyl)-1H-isoindole-1,3-(2H)-dione 2-(5-Hydroxymethyl-2-furanylmethyl)-1H-isoindole-1,3(2H)-dione (10 g) was dissolved in thionyl chloride (15 ml) with the aid of gentle heat. The solution was evaporated to dryness and the solid residue re-evaporated with cyclohexanebenzene (1:1). The residue was suspended in ether, the suspension filtered, washed with ether and dried to give 2-(5-chloromethyl-2-furanylmethyl)-1H-isoindole-1,3(2H)-dione (10.1 g) m.p. 119°–122° (dec.). Analysis Found: C, 61.32; H, 3.71; N, 5.00. $C_{14}H_{10}ClNO_4$ requires: C, 60.99; H, 3.66; N, 5.08%.

N"-Cyano-N-[2-[[5-[(1,3-dioxo-2H-isoindol-2-yl)methyl]-2-furanylmethyl]thio]ethyl]-N'-methylguanidine To a stirred solution of N"-cyano-N-(2-mercaptoethyl)-N'-methylguanidine (1.0 g) and sodium hydride (0.152 g) in dry dimethylformamide (4 ml) at room temperature was added slowly a solution of 2-(5-chloromethyl-2-furanylmethyl)-1H-isoindole-1,3(2H)-dione (1.74 g) in dry dimethylformamide (8 ml). After stirring for 2 hr in the solution was evaporated to dryness and the oily residue suspended in an ethyl acetate (25 ml)-water (20 ml) mixture. The solid residue was filtered and crystallised from methanol to give the title compound (1.4 g) m.p. 179°–182°.

N-[2-[[5-(Aminomethyl)-2-furanylmethyl]thio]ethyl]-N"-cyano-N'-methylguanidine

A suspension of N"-cyano-N-[2-[[5-[(1,3-dioxo-2H-isoindol-2-yl)methyl]-2-furanylmethyl]thio]ethyl]-N'-methylguanidine (4.45 g) and hydrazine hydrate (0.6 g) in methanol (35 ml) was heated under reflux for 4 hr. The suspension was evaporated to dryness, the residue dissolved in water (15 ml) at 0° and neutralised with 5 N hydrochloric acid. The suspension was filtered, excess anhydrous sodium carbonate added and the solution evaporated to dryness. The residue was mixed with anhydrous sodium sulphate and the solid mass extracted with ethanol. Evaporation of the extract gave a semi-solid which was mixed with anhydrous sodium sulphate and extracted with ethyl acetate to give an oil (2.12 g) which was column chromatographed (silica/methanol:0.88 ammonia 79:1). Evaporation of the relevant eluate yielded an oil which slowly solidified consisting of the title compound (1.88 g) m.p. 80°–82°. Analysis Found: C, 49.57; H, 6.66; N, 25.93. $C_{11}H_{17}N_5OS$ requires: C, 49.41; H, 6.41; N, 26.20%.

EXAMPLE 20

N-[2-[[[5-(Dimethylamino)methyl-2-furanyl]methyl]thio]ethyl]-N'-methyl-2-nitro-1,1-ethanediamine 2-Nitroethylene thiazolidine A mixture of cysteamine hydrochloride (11.36 g), potassium hydroxide (5.61 g) and 1,1-bis(methylthio)-2-nitroethane (16.52 g) in water (30 ml) and ethanol (100 ml) was heated under reflux for 1 hr. The suspension was evaporated to dryness, the residue suspended in water, filtered and the residue crystallised from methanol to give 2-nitroethylene thiazolidine (9.2 g) m.p. 141°–142°. Analysis Found: C, 32.91; H, 4.13; N, 19.10. $C_4H_6N_2O_2S$ requires: C, 32.87; H, 4.14; N, 19.17%.

N-(2-Mercaptoethyl)-N'-methyl-2-nitro-1,1-ethenediamine

A solution of 2-nitroethylene thiazolidine (5 g) in a solution of methylamine 33% in ethanol (40 ml) was kept at room temperature for 65 hr. The solid which separated was filtered, washed with ethanol and dried to give N-(2-mercaptoethyl)-N'-methyl-2-nitro-1,1'-ethenediamine (4.98 g), m.p. 174°–175°, decomp. 209°–211°. Analysis Found: C, 34.05; H, 5.87; N, 23.85. $C_5H_{11}N_3O_2S$ requires C, 33.88; H, 6.26; N, 23.71%.

N-[2-[[[5-(Dimethylamino)methyl-2-furanyl]methyl]thio]ethyl]-N'-methyl-2-nitro-1,1-ethenediamine N-(2-Mercaptoethyl)-N'-methyl-2-nitro-1,1-ethenediamine (354 mg) in concentrated hydrochloric acid (2 ml) was added dropwise to 5-(dimethylamino)- methyl-2-furanmethanol (428 mg) at 0°. After standing at 0° for 7 days the reaction was diluted with water (3 ml), excess potassium carbonate was added and the solid extracted with ethyl acetate (50 ml).

The solvent was evaporated and the residue purified by preparative layer chromatography to give the title compound (100 mg) as Example 15.

EXAMPLE 21

N-[2-[[[5-(Dimethylamino)methyl-2-furanyl]methyl]thio]ethyl]-N'-methyl-2-nitro-1,1-ethenediamine N,N-Dimethyl-2-furanmethanamine (125 mg) was dissolved in glacial acetic acid (1 ml) and paraformaldehyde (30 mg) added. A solution of N-(2-mercaptoethyl)-N'-methyl-2-nitro-1,1-ethenediamine (354 mg) in concentrated hydrochloric acid (1 ml) and glacial acetic acid (1 ml) was added dropwise and the mixture left to stand at room temperature for 5 days. The solution was diluted with water (30 ml), saturated with potassium carbonate and extracted with ethyl acetate. The combined extracts were purified by preparative layer chromatography to give the title compound as Example 15 (89 mg).

EXAMPLE 22

N-Cyano-N'-[2-[[[5-(dimethylamino)methyl-2-furanyl]methyl]thio]ethyl]-N''-methylguanidine N-Cyano-N'-[2-[[[5-(dimethylamino)methyl-2-furanyl]methyl]thio]ethyl]carbadmimidothioic acid, methyl ester 2-[[[5-(Dimethylamino)methyl-2-furanyl]methyl]thio]ethanamine (1.07 g) was added to a solution of N-cyanoimidocarbamodithioic acid, dimethyl ester (0.73 g) in ether, and stirred overnight. The crystalline solid which formed was filtered, washed with ether and dried to give N-cyano-N'-[2-[[[5-(dimethylamino)methyl-2-furanyl]methyl]thio]ethyl]carbamimidothioic acid, methyl ester (1.14 g) m.p. 78°–79°.

N-Cyano-N'-[2-[[[5-(dimethylamino)methyl-2-furanyl]methyl]thio]ethyl]-N''-methylguanidine A solution of N'-cyano-N-[2-[[[5-(dimethylamino)methyl-2-furanyl]methyl]thio]ethyl]carbamimidothioic acid, methyl ester (1.06 g) in ethanolic methylamine 33% (10 ml) was stirred at room temperature for 4 hr. The solution was evaporated to dryness and the oily residue crystallised from ethyl acetate-light petroleum (b.p. 80°–100°) to give the title compound m.p. 77°–80°.

EXAMPLE 23

N-Cyano-N'-[2-[[[5-(dimethylamino)methyl-2-furanyl]methyl]thio]ethyl]-N''-heptylguanidine A mixture of heptylamine (1.15 g) and N-cyano-N'-[2-[[[5-(dimethylamino)methyl-2-furanyl]methyl]thio]ethyl]carbamimidothioic acid (3.12 g) was heated on an oil bath for 12 hr at 100°. The product was chromatographed (silica/methanol) to give N-cyano-N'-[2-[[[5-dimethylamino)methyl-2-furanyl]methyl]thio]ethyl]-N''-heptylguanidine hydrate (2.31 g) Rf 0.49. Analysis Found: C, 56.99; H, 8.32; N, 17.53. $C_{19}H_{33}N_5OS \cdot H_2O$ requires: C, 57.43; H, 8.81; N, 17.63%.

EXAMPLE 24

N-[2-[[[5-(Dimethylamino)methyl-2-furanyl]methyl]thio]ethyl]-N'-methyl-2-nitro-1,1-ethenediamine 2-[[[5-(Dimethylamino)methyl-2-furanyl]methyl]thio]ethanamine (4.25 g) and 1,1-bis(methylthio)-2-nitroethene (3.3 g) were refluxed in acetonitrile (50 ml) for 14 hr. Solvent was removed and the residue dissolved in 36% methanolic methylamine (50 ml) and the solution refluxed for 8 hr. Solvents were removed and the residue in methanol treated with charcoal. Filtration and evaporation of the solvent gave the title compound as Example 15 (5.0 g).

EXAMPLE 25

(a)

N-[2-[[[5-(Dimethylamino)methyl-2-furanyl]methyl]thio]ethyl]-N'-(2-methoxyethyl)-2-nitro-1,1-ethenediamine 2-[[[5-(Dimethylamino)methyl-2-furanyl]methyl]thio]ethanamine (2.14 g) and 1,1-bis(methylthio)-2-nitroethane (1.65 g) were refluxed in acetonitrile for 8 hr. Solvents were removed and an ethanolic solution of 2-methoxyethylamine (0.75 g) added. After refluxing for a further 8 hr, removal of solvents gave an oil. This was purified by column chromatography to give N-[2-[[[5-(dimethylamino)methyl-2-furanyl]methyl]thio]ethyl]-N'-(2-methoxyethyl)-2-nitro-1,1-ethenediamine (1.0 g). NMR $\tau(CDCl_3)$ 7.73 s (6H); 7–7.5 m (2H); 6.2–7 m (11H); 6.23 s (2H); 3.81 s (2H); 3.42 s (1H).

Similarly prepared was:

(b) N-[2-[[[5-(Dimethylamino)methyl-2-furanyl]methyl]thio]ethyl]-2-nitro-1,1-ethenediamine, m.p. 100°–101°.

EXAMPLE 26

(a)

N-[4-[5-(Dimethylamino)methyl-2-furanyl]butyl]-N'-methyl-2-nitro-1,1-ethenediamine 4-[5-(Dimethylamino)methyl-2-furanyl]butanamine (0.7 g) and 1,1-bis(thiomethyl)-2-nitroethene (0.6 g) in acetonitrile (12 ml) were refluxed for 22 hr. Solvent was removed and the residue in 33% ethanolic methylamine refluxed for 2 hr. Solvents were removed and the residue purified by column chromatography (silica/methanol) to give N-[4-[5-(dimethylamino)methyl-2-furanyl]butyl]-N'-methyl-2-nitro-1,1-ethenediamine (310 mg). Analysis Found: C, 55.54; H, 8.23; N, 17.75. $C_{14}H_{24}N_4O_3 \cdot \frac{1}{4}H_2O$ requires: C, 55.26; H, 8.22; N, 18.42%.

Similarly prepared were:

(b) N-[5-[5-(Dimethylamino)methyl-2-furanyl]pentyl]-N'-methyl-2-nitro-1,1-ethenediamine. Analysis Found: C, 56.76; H, 8.36; N, 17.37. $C_{15}H_{26}N_4O_3 \cdot \frac{1}{4}H_2O$ requires: C, 56.43; H, 8.46; N, 17.55%.

(c) N-[3-[[5-(Dimethylamino)methyl-2-furanyl]thio]propyl]-N'-methyl-2-nitro-1,1-ethenediamine. Analysis Found: C, 49.36; H, 7.19; N, 17.45. $C_{13}H_{22}N_4O_3S$ requires: C, 49.66; H, 7.05; N, 17.84%.

(d) N-[3-[5-(Dimethylamino)methyl-2-furanyl]propyl]-N'-methyl-2-nitro-1,1-ethenediamine. Analysis Found: C, 55.09; H, 7.84; $C_{13}H_{22}N_4O_3$ requires: C, 55.31; H, 7.72%.

(e) N-[2-[[[5-(Diethylamino)methyl-2-furanyl]methyl]thio]ethyl]-N'-methyl-2-nitro-1,1-ethenediamine. Analysis Found: C, 51.38; H, 7.44; N, 15.66.

$C_{15}H_{26}N_4O_3S \cdot \frac{1}{2}H_2O$ requires: C, 51.26; H, 7.74; N, 15.94%.

(f) N-[3-[[[5-(Dimethylamino)methyl-2-furanyl]methyl]thio]propyl]-N'-methyl-2-nitro-1,1-ethenediamine. Analysis Found: C, 49.57; H, 7.20; N, 15.59. $C_{14}H_{24}N_4O_3S \cdot \frac{1}{2}H_2O$ requires: C, 49.86; H, 7.47; N, 16.61%.

EXAMPLE 27

(a)

N-Cyano-N'-[4-[5-(dimethylamino)methyl-2-furanyl]butyl]-N''-methylguanidine

4-[5-(Dimethylamino)methyl-2-furanyl]butanamine (0.4 g) and N-cyanoimidocarbamodithioic acid, dimethyl ester (0.3 g) were stirred in ethanol at room temperature for 3 hr. A solution of 33% methylamine in ethanol was then added and the mixture heated under reflux for 2 hr. Solvent was removed under reduced pressure and the product purified by column chromatography (silica/methanol) to give the product as a pale yellow oil. NMR $\tau(CDCl_3)$ 8-8.5 br (4H); 7.77 s (6H); 6.61-7.5 m (9H); 4.0 m (2H); 2.8-3.7 m (2H).

In a similar manner were prepared:

(b) N-Cyano-N'-[5-[5-(dimethylamino)methyl-2-furanyl]pentyl]-N'-methyl guanidine. NMR $\tau(CDCl_3)$ 8.0-8.7 br (6H); 7.67 s (6H); 7.32 t (2H); 7.10 d (3H); 6.7 q (2H); 6.48 s (2H); 3.8-4.3 m (4H).

EXAMPLE 28

(a)

N-[2-[[[5-(Dimethylamino)methyl-2-furanyl]methyl]thio]ethyl]-N'-methanesulphonyl-N''-methylguanidine Methanesulphonyliminodithiocarbamic acid, dimethyl ester (1.9 g) and 2-[[[5-(dimethylamino)methyl-2-furanyl]methyl]thio]ethanamine (2.14 g) were stirred in ethanol at room temperature for 3 hr. 33% Ethanolic methylamine (20 ml) was added and the whole heated under reflux for 16 hr. The product was purified by column chromatography (silica/methanol) to give N-[2-[[[5-(dimethylamino)methyl-2-furanyl]methyl]thio]ethyl]-N'-methanesulphonyl-N''-methylguanidine as a pale oil (2.7 g). Found: C, 43.54; H, 7.05; N, 15.48. $C_{13}H_{24}N_4O_3S_2 \cdot \frac{1}{2}H_2O$ requires: C, 43.70; H, 7.00; N, 15.69%.

Similarly prepared was:

(b) N-Benzenesulphonyl-N'-[2-[[[5-(dimethylamino)methyl-2-furanyl]methyl]thio]ethyl]-N''-methylguanidine. Analysis Found: C, 50.30; H, 6.25; N, 12.93. $C_{18}H_{26}N_4O_3S \cdot H_2O$ requires: C, 50.47; H, 6.54; N, 13.08%.

EXAMPLE 29

N-Cyano-N'-[2-[[[5-(dimethylamino)methyl-2-furanyl]methyl]thio]ethyl]-N''-methylguanidine A solution of silver nitrate (8.25 g) in dimethylformamide (50 ml) was added dropwise to a solution of N-cyano-N'-methylcarbamimidothioic acid, methyl ester (6.1 g), triethylamine (4.8 g) and 2-[[[2-furanyl]methyl]thio]ethanamine (7.8 g) in methanol (150 ml). After 42 hr at 50° the mixture was filtered and the filtrate evaporated. The residue was partitioned between ethyl acetate and water. The organic layers were dried and evaporated to give an oil which yielded crystalline N-cyano-N'-[2-[[[2-furanyl]methyl]thio]ethyl]-N''-methylguanidine (3.9 g) m.p. 78°-82°.

A solution of this amine (4.5 g), dimethylamine hydrochloride (3.1 g) and 36% aqueous formaldehyde (3.16 g) in ethanol (20 ml) was heated at 50° for 60 hr. The residue was partitioned between ethyl acetate and aqueous base. The organic extracts were combined, dried and evaporated to give an oil which on treatment with sebacic acid in isopropanol gave the sebacic acid salt of the title compound (2 g) m.p. 93°-94°.

EXAMPLE 30

N-[2-[[[5-(Dimethylamino)methyl-2-furanyl]methyl]thio]ethyl]-N'-methylthiourea

Carbon disulphide (1.52 g) was added with stirring to a cooled solution of sodium hydroxide (0.8 g) in water (1.7 ml). 2-[[[5-(Dimethylamino)methyl-2-furanyl]methyl]thio]ethanamine (4.28 g) was added slowly and when addition was complete the mixture heated at 100° for 2 hr. After cooling to below 40° ethyl chloroformate (1.94 ml) was added and stirring continued for a further 30 mins. The lower thick yellow oil was extracted with chloroform, dried and evaporated to give N,N-dimethyl-5-[[[2-(isothiocyanato)ethyl]thio]methyl]furanmethanamine as an oil RF 0.43 (silica/methanol).

The crude isothiocyanate (0.46 g) was dissolved in 33% ethanolic methylamine (25 ml), left to stand overnight and N-[2-[[[5-(dimethylamino)methyl-2-furanyl]methyl]thio]ethyl]-N'-methylthiourea isolated as a pale oil (0.16 g) identical to material prepared from 2-[[[5-(dimethylamino)methyl-2-furanyl]methyl]thio]ethanamine and methyl isothiocyanate.

EXAMPLE 31

N-Cyano-N'-[2-[[[5-(dimethylamino)methyl-2-furanyl]methyl]thio]ethyl]-N''-methylguanidine A solution of N-[2-[[[5-(dimethylamino)methyl-2-furanyl]methyl]thio]ethyl]-N'-methylthiourea (1.3 g) was heated at reflux with lead cyanamide (1.5 g). The solution was filtered and the filtrate evaporated. Treatment of the residue with a solution of sebacic acid in isopropanol gave the title compound as its monosebacate salt (0.7 g) m.p. 90°-92°.

EXAMPLE 32

N-[2-[[[5-(Dimethylamino)methyl-2-furanyl]methyl]thio]ethyl]-N'-methyl-2-nitro-1,1-ethenediamine hydrochloride N-[2-[[[5-(Dimethylamino)methyl-2-furanyl]methyl]thio]ethyl]-N'-methyl-2-nitro-1,1-ethenediamine (50 g, 0.16 mole) was dissolved in industrial methylated spirit 74° o.p. (200 ml) containing 0.16 of an equivalent of hydrogen chloride. Ethyl acetate (200 ml) was added slowly to the solution. The hydrochloride crystallised and was filtered off, washed with a mixture of industrial methylated spirit 74° o.p. (50 ml) and ethyl acetate (50 ml) and was dried at 50°. The product (50 g) was obtained as an off-white solid m.p. 133°-134°.

EXAMPLE 33

Pharmaceutical Compositions

| (a) Oral Tablets 50 mg | for 10,000 tablets |
|---|---|
| Active ingredient | 500 g |
| Anhydrous lactose U.S.P. | 2.17 kg |
| Sta-Rx 1500 Starch* | 300 g |
| Magnesium Stearate B.P. | 30 g |

*A form of directly compressible starch, supplied by A.E. Staley Mfg. Co. (London) Limited, Orpington, Kent.

The drug is sieved through a 250 μm sieve and then the four powders are intimately mixed in a blender and compressed between 8.5 mm diameter punches in a tabletting machine.

| (b) Injection for Intravenous administration (200 mg in 2 ml) | | |
|---|---|---|
| | | % w/w |
| Active ingredient | | 10.0 |
| Water for Injections BP | to | 100.0 |
| Dilute hydrochloric acid BP | to | pH 5.0 |

The active ingredient is dissolved with mixing in the Water for Injections, adding the acid slowly until the pH is 5.0. The solution is sparged with nitrogen and is then clarified by filtration through a membrane filter of pore size 1.35 μm. It is packed into 2 ml glass ampoules (2.2 ml in each) and each ampoule sealed under an atmosphere of nitrogen. The ampoules are sterilised in an autoclave at 121° for thirty minutes.

| (c) Oral Sustained Release Tablets 150 mg | |
|---|---|
| | for 10,000 tablets |
| Active ingredient | 1.50 kg |
| Cutina HR** | 0.40 kg |
| Anhydrous lactose U.S.P. | 2.060 kg |
| Magnesium Stearate BP | 40g |

**Cutina HR is a grade of microfine hydrogenated castor oil supplied by Sipon Products Limited, London The active ingredient, Anhydrous lactose and most of the Cutina HR are intimately mixed and then the mixture is moistened by mixing with a 10% solution of the remainder of the Cutina HR in Industrial Methylated Spirit OP 74. The moistened mass is granulated through a 1.2 mm aperture sieve and dried at 50° C. in a fluidised bed dryer. The granules are then passed through a 0.85 mm aperture sieve, blended with the magnesium stearate and compressed to a hardness of at least 10 kg (Schleuniger tester) on a tabletting machine with 12.5 mm diameter punches.

| (d) Oral Syrup | % w/v |
|---|---|
| Active ingredient | 2.0 |
| Dilute hydrochloric acid BP, as required | |
| Sorbitol Solution BPC | 60 v/v |
| Flavour | as required |
| Distilled water | to 100 |

The drug is dissolved in some of the water with stirring by adding gradually hydrochloric acid until the pH has fallen to 5.0. The Sorbitol Solution, flavour and the rest of the water are added and the pH re-adjusted to 5.0. The syrup is clarified by filtration through suitable cellulosic filter pads.

| (e) Oral Capsules 50 mg | for 10,000 capsules |
|---|---|
| Active ingredient | 500 g |
| Sta-Rx 1500* | 1700 g |
| Magnesium Stearate BP | 20 mg |

*A form of directly compressible starch, supplied by A.E. Staley Mfg. Co. (London) Limited, Orpington, Kent The drug is sieved through a 250 μm mesh sieve and is then blended with the other powders. The powder is filled into No. 3 size hard gelatin capsules on a suitable filling machine.

| (f) Ointment | % by weight |
|---|---|
| Active ingredient | 2.0 |
| White Soft Paraffin BP | to 100 |

The drug is sieved through a 150 μm aperture sieve and is then uniformly blended with the White Soft Paraffin in a high shear mixer.

| (g) Cream | % by weight |
|---|---|
| Active ingredient | 2.0 |
| Cetomacrogol Emulsifying Ointment BP | 30.0 |
| Chlorocresol | 0.1 |
| Distilled water | to 100 |

The drug is passed through a 150 μm aperture sieve and is then blended intimately with the Cetomacrogol Emulsifying Ointment at 65° C. The chlorocresol is dissolved in the water at 65° C. and this solution is then mixed with the oily drug mixture and the resulting emulsion is stirred continuously during cooling to give a cream.

The active ingredient is a compound according to the invention. Particular examples are the compounds of Example 10 and Example 15. Other compounds according to the invention may also be used.

The compounds of the formula (I) have been found to be inhibitors of gastric acid secretion induced by histamine. This has been shown in rats using a modification of the procedure described by M. N. Ghosh and H. O. Schild in the British Journal of Pharmacology 1958, Vol. 13, page 54.

Female rats weighing about 150 g are starved overnight and provided with 8% sucrose in normal saline instead of drinking water.

The rats are anaesthetized by a single intraperitoneal injection of 25% w/v urethane solution (0.5 ml/100 g) and the trachea and jugular veins cannulated.

A mid-line incision in the abdomen wall is made to expose the stomach which is separated from the liver and spleen by cutting the connective tissue. A small opening is made in the fundic region of the stomach and the stomach washed with a 5% dextrose solution. The oesophagus is cannulated with rubber tubing and the oesophagus and vagi are then cut above the cannula.

A small opening is then made in the pyloric region of the stomach. A large perspex cannula is then placed in the stomach via the opening in the fundic region in such a manner that the inlet end of the cannula passes out of the stomach through the opening in the pyloric region. The cannula is of such a shape so as to reduce the effective volume of the stomach and to provide a turbulent flow of the perfusion fluid over the mucosal surface. A drainage cannula is then inserted through the opening in the fundic region of the stomach. Both cannulae are tied in place by ligatures around the stomach, positioned to avoid the main blood vessels. Stab wounds are made in the body wall and the cannulae passed through. The stomach is perfused through the oesophageal and pyloric cannulae with 5% dextrose solution at 39° C. at a rate of 1.5 ml/min. for each cannula. The effluent is passed over a micro-flow pH electrode and recorded via a pH meter and flat bed recorder.

The basal output of acid secretion from the stomach is monitored by measurement of the pH of the perfusion effluent and then increased acid secretion is induced by a continuous intravenous infusion of a sub-maximal dose of histamine; this produces a stable plateau of acid secretion and the pH of the perfusion effluent is determined when this condition is obtained.

The test compound is then administered to the rat by an intravenous injection and the change in 'gastric' acid secretion is monitored by measuring the change in the pH of the perfusion effluent.

From the change in pH of the perfusion effluent, the difference in acid secretion between basal output and the histamine stimulated plateau level is calculated as hydrogen ion concentration in mole/L. The reduction of acid secretion caused by the administration of the test compound is also calculated as the change in hydrogen ion concentration in mole/L from the difference in the pH of t perfusion effluent. The percentage reduction in acid secretion caused by the administration of the test compound may then be calculated from the two figures obtained.

$ED_{50}$ values for inhibition of acid secretion are determined by administering one dose of the test compound to one rat and repeating this in at least four rats for each of three or more dose levels. The results obtained are then used to calculate the $ED_{50}$ value by the standard method of least squares, as used for any dose response line.

Using the above procedure the following $ED_{50}$s were obtained:

| Compound of Example No. | $ED_{50}$ mg/kg |
|---|---|
| 2(c) | 1.5 |
| 8 | 0.65 |
| 9(a) | 2.30 |
| 10 | 1.39 |
| 14(a) | 0.23 |
| 14(f) | 0.8 |
| 14(h) | 0.48 |
| 15 | 0.18 |
| 25(a) | 1.82 |
| 26(a) | 0.55 |

What is claimed is:

1. A compound of the general formula I:

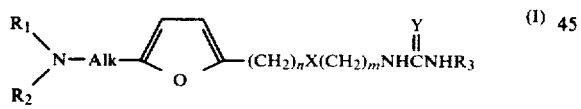

or a physiologically acceptable acid addition salt, N-oxide or hydrate thereof, in which $R_1$ and $R_2$ together with the nitrogen atom to which they are attached, form a 5- or 6-membered saturated heterocyclic ring selected from the group consisting of morpholino, piperidino, pyrrolidino, and N-alkylpiperazino;

$R_3$ is hydrogen, lower alkyl, lower alkenyl or alkoxyalkyl; X is —$CH_2$—, —O— or —S—;

Y represents =S, =O, =$NR_5$ or =$CHR_6$;

Alk denotes a straight or branched alkylene chain of 1 to 6 carbon atoms;

$R_5$ is H, nitro, cyano, lower alkyl, phenyl, phenyl substituted by alkyl, alkoxy or halogen, alkylsulphonyl, or arylsulphonyl in which the aryl moiety is phenyl or phenyl substituted by alkyl, alkoxy or halogen;

$R_6$ represents nitro, arylsulphonyl in which the aryl moiety is phenyl or phenyl substituted by alkyl, alkoxy or halogen, or alkylsulphonyl;

m is an integer from 2 to 4; and n is 1 or 2; or when X is —S— or —$CH_2$—, n is zero, 1 or 2.

2. A compound as claimed in claim 1 in which Alk represents a straight alkylene chain of 1 to 4 carbon atoms, Y is =S, =O, =$CHNO_2$ or =$NR_5$ where $R_5$ is hydrogen, nitro, cyano, lower alkyl, alkylsulphonyl or benzenesulphonyl, and X, m, n, and $R_3$ having the meanings given in claim 1.

3. A compound as claimed in claim 1 in which the lower alkyl groups have 1 to 8 carbon atoms.

4. A compound as claimed in claim 1 in which the alkenyl groups have 3 to 6 carbon atoms.

5. A compound as claimed in claim 1 in which n+m is 3 or 4.

6. A compound as claimed in claim 1 in which Alk represents a methylene group.

7. A compound as claimed in claim 1 in which X is a sulphur atom.

8. A compound as claimed in claim 1 in which X represents a group —$CH_2$—.

9. A compound as claimed in claim 1 in which $R_1$ and $R_2$ together with the nitrogen atom form a pyrrolidine ring; Alk represents an alkylene chain of 1 to 3 carbon atoms; Y is =S, =$CHNO_2$, or =$NR_5$, where $R_5$ is nitro, cyano, methylsulphonyl or benzenesulphonyl; $R_3$ represents hydrogen, alkyl of 1 to 3 carbon atoms, propenyl or alkoxyalkyl of 3 carbon atoms; n+m is 3 or 4, and X is as defined in claim 1.

10. A compound as claimed in claim 1 in which $R_1$ and $R_2$ together with the nitrogen atom form a pyrrolidine ring; Alk represents an alkylene group of 1 to 3 carbon atoms; Y is =S, =$CHNO_2$, or =$NR_5$, where $R_5$ is nitro, cyano, methylsulphonyl or benzenesulphonyl; X is S or —$CH_2$—; $R_3$ is hydrogen, methyl or methoxyethyl; n is 1 and m is 2 or 3.

11. A compound as claimed in claim 1 which is a hydrochloride.

12. A compound as claimed in claim 1 in which $R_1$ and $R_2$ together with the nitrogen atom to which they are attached are pyrrolidinyl.

13. The compound of claim 1 which is N-methyl-N'-[2-[[[5-(1-pyrrolidinyl)methyl-2-furanyl]methyl]thio]ethyl]thiourea.

14. The compound of claim 1 which is N-methyl-N'-[2-[[[5-(1-pyrrolidinyl)methyl-2-furanyl]methyl]thio]ethyl]urea.

15. The compound of claim 1 which is N-cyano-N'-[2-[[[5-(1-pyrrolindinyl)methyl-2-furanyl]methyl]thio]ethyl]-N''-methylguanidine.

16. The compound of claim 1 which is N-methyl-2-nitro-N'-[2-[[[5-[(1-pyrrolidinyl)methyl]-2-furanyl]methyl]thio]ethyl]-1,1-ethenediamine.

17. A pharmaceutical composition for treating a condition mediated through histamine $H_2$-receptors, comprising a pharmaceutically effective amount of a compound as claimed in claim 1 in association with a pharmaceutically acceptable carrier or diluent.

18. A composition as claimed in claim 17 in a form suitable for oral, topical or parenteral administration or administration by suppository.

19. A composition as claimed in claim 18 in oral form as tablets.

20. A composition as claimed in claim 19 in the form of slow release tablets.

21. A composition as claimed in claim 19 containing 20 to 200 mg of active ingredient per tablet.

22. A composition as claimed in claim 18 in topical form as a spray, ointment or cream.

23. A method of treating a condition mediated through histamine $H_2$-receptors which comprises administering to a patient an effective amount of a compound as claimed in claim 1 to relieve said condition.

24. A method as claimed in claim 23 in which the condition is peptic ulceration.

25. A method as claimed in claim 23 in which the condition is an allergic skin condition.

* * * * *